United States Patent
Nakamura et al.

(10) Patent No.: US 10,059,686 B2
(45) Date of Patent: Aug. 28, 2018

(54) COMPOUND USEFUL FOR MANUFACTURING SALACINOL, METHOD FOR MANUFACTURING THE COMPOUND, METHOD FOR MANUFACTURING SALACINOL, METHODS FOR PROTECTING AND DEPROTECTING DIOL GROUP, AND PROTECTIVE AGENT FOR DIOL GROUP

(71) Applicant: FUJIFILM Corporation, Minato-ku, Tokyo (JP)

(72) Inventors: Koki Nakamura, Ashigarakami-gun (JP); Hisato Nagase, Ashigarakami-gun (JP); Yuuta Fujino, Ashigarakami-gun (JP); Katsuyuki Watanabe, Ashigarakami-gun (JP); Taiji Katsumata, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/709,794

(22) Filed: Sep. 20, 2017

(65) Prior Publication Data

US 2018/0009777 A1 Jan. 11, 2018

Related U.S. Application Data

(60) Division of application No. 15/268,829, filed on Sep. 19, 2016, now Pat. No. 9,802,913, which is a continuation of application No. PCT/JP2015/058197, filed on Mar. 19, 2015.

(30) Foreign Application Priority Data

Mar. 20, 2014 (JP) ................. 2014-057961

(51) Int. Cl.
| | |
|---|---|
| *C07D 333/46* | (2006.01) |
| *C07D 319/06* | (2006.01) |
| *C07D 409/06* | (2006.01) |
| *C07D 493/04* | (2006.01) |
| *C07D 497/04* | (2006.01) |
| *C07C 69/734* | (2006.01) |
| *C07D 317/30* | (2006.01) |
| *C07D 333/32* | (2006.01) |

(52) U.S. Cl.
CPC .......... *C07D 333/46* (2013.01); *C07C 69/734* (2013.01); *C07D 317/30* (2013.01); *C07D 319/06* (2013.01); *C07D 333/32* (2013.01); *C07D 409/06* (2013.01); *C07D 493/04* (2013.01); *C07D 497/04* (2013.01); *Y02P 20/55* (2015.11)

(58) Field of Classification Search
CPC .................................................. C07D 333/46
USPC ........................................................ 549/15
See application file for complete search history.

(56) References Cited

U.S. PATENT DOCUMENTS 5,817,639 A 10/1998 Watanabe et al.

FOREIGN PATENT DOCUMENTS

| CN | 1404476 A | 3/2003 |
|---|---|---|
| DE | 195 25 314 A1 | 1/1997 |
| JP | H 09-249690 A | 9/1997 |
| JP | 3030008 B2 | 4/2000 |
| JP | 2002-179673 A | 6/2002 |
| JP | 4939934 B2 | 5/2012 |
| JP | 5053494 B2 | 10/2012 |
| WO | 01/49674 A2 | 7/2001 |
| WO | 01/49674 A3 | 7/2001 |
| WO | 2004/113289 A2 | 12/2004 |
| WO | 2004/113289 A3 | 12/2004 |

OTHER PUBLICATIONS

Office Action dated Mar. 27, 2018 from the Japanese Patent Office in counterpart Japanese application No. 2017-168471.
A. Ilangovan et al "2,2-Bis(ethoxycarbonyl)vinyl (BECV) as a Versatile Amine Protecting Group for Selective Functional-Group Transformations", Chemistry—A European Journal vol. 16, Issue 9; Mar. 1, 2010 (3 pages total).
Antonio Gomez-Sanchez et al. "Synthesis and Glycosidation of 1-Deoxy-1-[(2,2-Diacyl-Vinyl)Amino]-D-Fructoses" Carbohydrate Research, vol. 149, No. 2 (1986); pp. 329-345.
Partial Supplementary European Search Report dated Dec. 2, 2016 from the European Patent Office in counterpart European Application No. 15765614.1.
Extended European Search Report dated Mar. 7, 2017, from the European Patent Office in counterpart European Application No. 15765614.1.
Greene T.W. et al., Protective Groups in Organic Synthesis, 3rd edition, 1999, p. 199.
Hubert Hrebabecky et al. "Synthesis of Carba Analogues of Deoxy-4-C-(hydroxymethyl) pentofuranoses, Intermediates in the Synthesis of Carbocyclic Nucleosides", Collect. Czech Chem. Commun. vol. 63, No. 12, pp. 2044-2064 (1998) (21 pages total).
(Continued)

*Primary Examiner* — Taofiq A Solola
(74) *Attorney, Agent, or Firm* — Sughrue Mion, PLLC

(57) ABSTRACT

An object of the present invention is to provide a novel compound useful for manufacturing salacinol, a method for manufacturing the compound, a method for manufacturing salacinol, methods for protecting and deprotecting a diol group, and a protective agent for a diol group. A compound represented by Formula (1) is a compound useful for manufacturing salacinol.

(1)

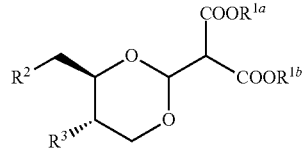

(In the formula, each of $R^{1a}$ and $R^{1b}$ is a hydrogen atom or a hydroxy protective group; $R^2$ is a hydroxy group or the like; and $R^3$ is a hydroxy group or the like.).

5 Claims, No Drawings

(56) References Cited

OTHER PUBLICATIONS

International Preliminary Report on Patentability with translation of Written Opinion dated Sep. 29, 2016, issued by the International Searching Authority in Application No. PCT/JP2015/058197.

International Search Report for PCT/JP2015/058197 dated Jun. 9, 2015.

Masayuki Yoshikawa et al., "Salacinol, Potent Antidiabetic Principle with Unique Thiosugar Sulfonium Sulfate Structure from the Ayurvedic Traditional Medicine *Salacia reticulata* in Sri Lanka and India", Tetrahedron Letters, 1997, pp. 8367-8370, vol. 38, No. 48.

Oliver Schulze et al., "The thio-Mitsunobu reaction: a useful tool for the preparation of 2,5-anhydro-2-thio- and 3,5-anhydro-3-thiopentofuranosides", Carbohydrate Research, 2004, pp. 1787-1802, vol. 339, No. 10, Scheme 1, 3-4.

Peter G. M. Wuts and Theodora W. Greene, "Protection for the Hydroxyl Group, Including 1,2- and 1,3-Diols", Greene's Protective Groups in Organic Synthesis, Fourth Edition, 2007, pp. 16-367 (total 176 pages).

Shinji Kato et al. "Fabrication of Multilayer Assemblies Based on a Boronate-Terminated Self-Assembled Monolayer", Langmuir 1998, vol. 14, No. 9 (pp. 2372-2377).

Written Opinion for PCT/JP2015/058197 dated Jun. 9, 2015.

Xavier Ariza et al., "New Protecting Groups for 1,2-Diols (Boc- and Moc-ethylidene). Cleavage of Acetals and Bases", Organic Letters, 2000, pp. 2809-2811, vol. 2, No. 18.

Protective Groups in Organic Synthesis, 4th edition, John Wiley & Sons, Inc. (2007).

Office Action dated Apr. 4, 2018 from the State Intellectual Property Office of the P.R.C. in counterpart Chinese application No. 201580015125.4.

COMPOUND USEFUL FOR MANUFACTURING SALACINOL, METHOD FOR MANUFACTURING THE COMPOUND, METHOD FOR MANUFACTURING SALACINOL, METHODS FOR PROTECTING AND DEPROTECTING DIOL GROUP, AND PROTECTIVE AGENT FOR DIOL GROUP

The present application is a Divisional of U.S. application Ser. No. 15/268,829, filed Sep. 19, 2016 which is a continuation of PCT/JP2015/58197 filed on Mar. 19, 2015 and claims priority under 35 U.S.C. § 119 of Japanese Patent Application No. 57961/2014 filed on Mar. 20, 2014, the disclosures of which are incorporated herein by reference

BACKGROUND OF THE INVENTION

1. Field of the Invention

The present invention relates to a compound useful for manufacturing salacinol and a method for manufacturing the compound. The present invention also relates to a method for manufacturing salacinol, methods for protecting and deprotecting a diol group, and a protective agent for a diol group.

2. Description of the Related Art

In traditional Indian medicine, Salacia reticulata which is a climbing tree of the genus Salacia is used for treating diabetes. Salacinol is a component contained in plants of the genus Salacia such as Salacia reticulata and has a strong α-glucosidase inhibitory activity (Tetrahedron Letters, Vol. 38, No. 48, pp. 8367-8370 (1997)). Salacinol is obtained from, for example, extracts of plants of the genus Salacia (JP3030008B). However, the supply of plants of the genus Salacia is small, and it is difficult to easily obtain the plants. Therefore, methods for manufacturing salacinol and analogs thereof by synthesis are being investigated in various ways (JP5053494B, JP4939934B, and JP2002-179673A).

JP5053494B describes a manufacturing method in which a cyclic sulfuric acid ester protected with a benzylidene group is reacted with a thioarabinitol derivative protected with a benzyl group.

JP4939934B describes a manufacturing method in which a cyclic sulfuric acid ester protected with a benzylidene group is reacted with a thioarabinitol derivative protected with a benzyl group.

JP2002-179673A describes a manufacturing method in which a cyclic sulfuric acid ester protected with an isopropylidene group is reacted with thio-D-arabinitol.

In a case where organic synthesis is performed using a compound having a functional group such as an amino group, a hydroxy group, or a carboxy group, in order to prevent the functional group from affecting the reaction, generally, the functional group is protected. Furthermore, in a case where the number of functional groups is 2 or greater, in order to selectively came only an intended functional group to react, other functional groups are protected.

A protective group not only needs to stably protect a target functional group but also needs to be easily removed if necessary. Therefore, in organic synthesis, it is important to deprotect only a protective group bonded to a specific functional group under appropriate conditions.

For example, as protective groups for an amino group, a hydroxy group, or a carboxy group, various protective groups have been developed (Protective Groups in Organic Synthesis, 4$^{th}$ edition, John Wiley & Sons, INC (2007)). Furthermore, as protective groups for a 1,2-diol group or a 1,3-diol group (hereinafter, referred to as a "diol group" in some cases), a cyclic acetal, a cyclic ketal, a cyclic orthoester, and the like are known.

As a protective group for a diol group, an alkoxycarbonylethylidene group is known (Organic Letters, Vol. 2. No. 18, pp. 2809-2811 (2000)).

Meanwhile, a method for manufacturing diethyl 2-(5-pentyl-1,3-dioxan-2-yl)malonate by reacting 2-(hydroxymethyl)heptanol with diethyl ethoxymethylene malonate in the presence of p-toluenesulfonic acid is known (DE19525314B).

SUMMARY OF THE INVENTION

The method described in JP5053494B has defects such as (1) it has a low yield, and (2) a complicated operation is required because a hydrogenation reaction is used as a deprotection reaction. This is not satisfactory method.

The method described in JP49399934B has defects such as (1) hexafluoroisopropanol harmful to humans and imposing a great environmental load is used as a reaction solvent. This is not a satisfactory method.

The method described is JP2002-179673A had defects such as (1) it has a low yield, and (2) the reaction time is long. This is not a satisfactory method.

Furthermore, as described in Organic Letters, Vol. 2, No. 18, pp. 2809-2811 (2000), for example, a diol group can be protected with an alkoxycarbonylethylidene group in the presence of a base. However, the deprotection reaction has defects such as (1) an excess of base is necessary, and (2) heating is required. In addition, the types of protective group for a diol group are less diverse than the types of protective group for a hydroxy group.

In DE19525314B, the obtained diethyl 2-(5-pentyl-1,3-dioxan-2-yl)malonate is then reduced and derivatized into other compounds. This method does not aim to protect a diol group.

The methods for manufacturing salacinol in the related art have problems such as (1) they have a low yield, (2) a complicated operation is required, (3) a solvent harmful to humans and imposing a great environmental load is used, and (4) the reaction time is long. Therefore, there is a strong demand for a better industrial manufacturing method of salacinol and methods for protecting and deprotecting a diol group.

An object of the present invention is to provide a novel compound useful for manufacturing salacinol and a novel method for manufacturing salacinol.

Another object of the present invention is to provide methods for protecting and deprotecting a diol group and a protective agent for a diol group that are useful for manufacturing salacinol or the like.

Under the circumstances described above, the inventors of the present invention repeated intensive investigation. As a result, they obtained knowledge that a compound represented by Formula (1) and a compound represented by Formula (7a) are intermediates useful for manufacturing salacinol. The inventory of the present invention also obtained knowledge that salacinol can be industrially manufactured from a compound represented by Formula (1a) and a compound represented by Formula (7a). Furthermore, the inventors of the present invention found methods for protecting and deprotecting a diol group that are useful for manufacturing salacinol or the like. Based on the above knowledge, the inventors accomplished the present invention.

The present invention provides the following.

[1] A compound represented by Formula (1),

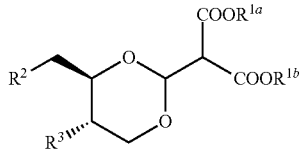 (1)

(in the formula, $R^{1a}$ and $R^{1b}$ are the same as or different from each other and each represent a hydrogen atom or a carboxy protective group; and each of $R^2$ and $R^3$ is a hydroxy group, $R^2$ is a group represented by Formula (2) and $R^3$ is a group represented by Formula (3),

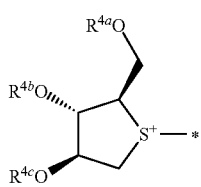 (2)

(in the formula, $R^{4a}$, $R^{4b}$, and $R^{4c}$ are the same as or different from each other and each represent a hydrogen atom or a hydroxy protective group; and * represents a binding position), and

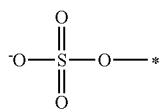 (3)

(in the formula, * has the same definition as described above), or $R^2$ and $R^3$ are bonded to each other and represent a group represented by Formula (4),

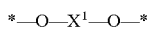 (4)

in the formula, $X^1$ is a group represented by Formula (5) or a group represented by Formula (6); and * has the same definition as described above),

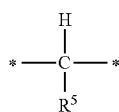 (5)

in the formula, $R^5$ is an aryl group which may be substituted; and * has the same definition as described above), and

 (6)

(in the formula, * has the same definition as described above)).

[2] The compound described in [1], in which $R^{1a}$ and $R^{1b}$ are the same as or different from each other and each represent a carboxy protective group.

[3] The compound described in [1] or [2], in which each of $R^2$ and $R^3$ is a hydroxy group.

[4] The compound described in [1] or [2], in which $R^2$ is a group represented by Formula 2); and $R^3$ is a group represented by Formula (3),

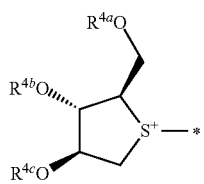 (2)

(in the formula, $R^{4a}$, $R^{4b}$, and $R^{4c}$ have the same definition as described above), and

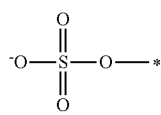 (3)

(in the formula, * has the same definition as described above).

[5] The compound described in [1] or [2], in which $R^2$ and $R^3$ are bonded to each other and represent a group represented by Formula (4),

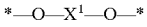 (4)

(in the formula, each of $X^1$ and * have the same definition as described above).

[6] The compound described in [1], [2], or [5], in which $R^5$ is a phenyl group which may be substituted.

[7] The compound described in [1] that is a compound selected from dimethyl 2-((4aS,8aR)-6-phenyltetrahydro[1,3]dioxino[5,4-d][1,3]dioxin-2-yl)malonate, dimethyl 2-((4R,5S)-5-hydroxy-4-(hydroxymethyl)-1,3-dioxan-2-yl)malonate, dimethyl 2-((4aR,8aS)-2,2-dioxidotetrahydrol[1,3]dioxino[5,4-d][1,3,2]dioxathiin-6-yl)malonate, (4S,5S)-4-(((2R,3S,4S)-3,4-dihydroxy-2-(hydroxymethyl)tetrahydro-1H-thiophen-1-ium-1-yl) methyl-2-(1,3-dimethoxy-1,3-dimethoxy-1,3-dioxopropan-2-yl)-1,3-dioxan-5-yl sulfate, (4S,5S)-4-(((1S,2R,3S,4S)-3,4-bis(benzyloxy)-2-((benzyloxy)methyl)tetrahydro-1H-thiophen-1-ium-1-yl)methyl-2-(1,3-dimethoxy-1,3-dioxopropan-2-yl)-1,3-dioxan-5-yl sulfate (4S,5S)-4-(((1S,2R,3S,4S)-3,4-bis(4-methoxybenzyl)oxy)-2-(((4-methoxybenzyl)oxy)methyl) tetrahydro-1H-thiophen-1-ium-1-yl)methyl)-2-(1,3-dimethoxy-1,3-dioxopropan-2-yl)-1,3-dioxan-5-yl sulfate, diethyl 2-((4aS,8aR)-6-phenyltetrahydro[1,3]dioxino[5,4-d][1,3]dioxin-2-yl)malonate, diethyl 2-((4R,5S)-5-hydroxy-4-

(hydroxymethyl)-1,3-dioxan-2-yl)malonate, diethyl 2-((4aR,8aS)-2,2-dioxidotetrahydro[1,3]dioxino[5,4-d][1,2,3]dioxathiin-6-yl)malonate, and (4S,5S)-2-(1,3-diethoxy-1,3-dioxopropan-2-yl)-4-(((2R,3S,4S)-3,4-dihydroxy-2-(hydroxymethyl)tetrahydro-1H-thiophen-1-ium-1-yl)methyl)-1,3-dioxan-5-yl sulfate.

[8] A method for manufacturing salacinol, comprising: obtaining a compound represented by Formula (1b) by reacting a compound represented by Formula (1a) with a compound represented by Formula (7),

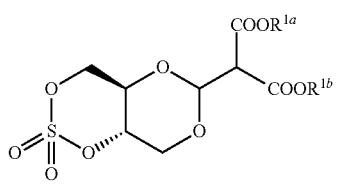
(1a)

(in the formula, each of $R^{1a}$ and $R^{1b}$ has the definition as described above),

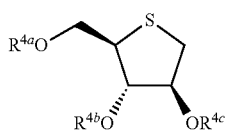
(7)

(in the formula, each of $R^{4a}$, $R^{4b}$, and $R^{4c}$ has the same definition as described above), and

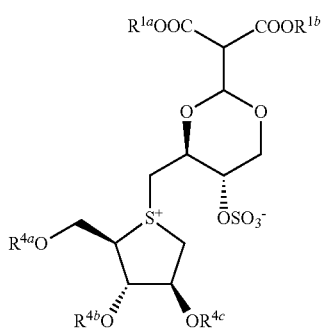
(1b)

(In the formula, each of $R^{1a}$, $R^{1b}$, $R^{4a}$, $R^{4b}$, and $R^{4c}$ has the same definition as described above); and then subjecting the compound represented by Formula (1b) to a deprotection reaction.

[9] The manufacturing method described in [8], in which each of $R^{1a}$ and $R^{1b}$ is a carboxy protective group; and each of $R^{4a}$, $R^{4b}$, and $R^{4c}$ is a hydrogen atom.

[10] A method for manufacturing salacinol, comprising: obtaining a compound represented by Formula (1c) by reacting a compound represented by Formula (8) with a compound represented by Formula (9),

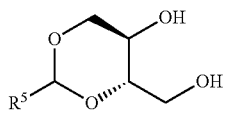
(8)

(in the formula, $R^5$ has the same definition as described above),

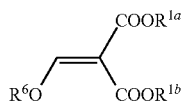
(9)

(in the formula, $R^6$ is a $C_{1-6}$ alkyl group which may be substituted; and each of $R^{1a}$ and $R^{1b}$ has the same definition as described above), and

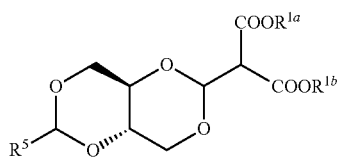
(1c)

(in the formula, each of $R^{1a}$, $R^{1b}$, and $R^5$ has the same definition as described above);
then obtaining a compound represented by Formula (1d) by subjecting the compound represented by Formula (1c) to a deprotection reaction,

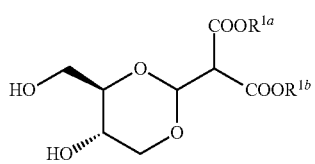
(1d)

(in the formula, each of $R^{1a}$ and $R^{1b}$ has the same definition as described above);
then obtaining a compound represented by Formula (1a) by reacting the compound represented by Formula (1d) with a sulfur-containing compound and then subjecting the resulting compound to an oxidation reaction if necessary,

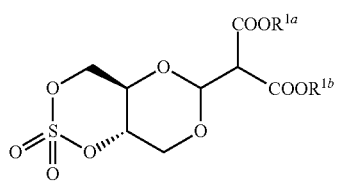
(1a)

(in the formula, each of $R^{1a}$ and $R^{1b}$ has the same definition as described above);
then, obtaining a compound represented by Formula (1b) by reacting the compound represented by Formula (1a) with a compound represented by Formula (7),

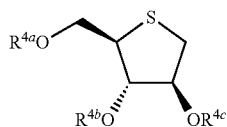
(7)

(in the formula, each of $R^{4a}$, $R^{4b}$, and $R^{4c}$ has the same definition as described above), and

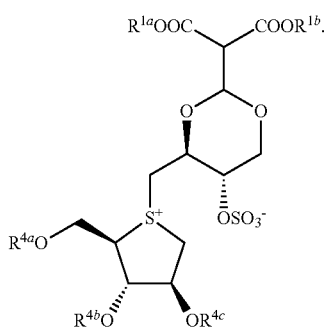
(1b)

(in the formula, each, of $R^{1a}$, $R^{1b}$, $R^{4a}$, $R^{4b}$, and $R^{4c}$ has the same definition as described above); and then subjecting the compound represented by Formula (1b) to a deprotection reaction.

[11] The manufacturing method described in [10], in which $R^5$ is a phenyl group which may be substituted.

[12] The manufacturing method described in [10] or [11], in which each of $R^{1a}$ and $R^{1b}$ is a carboxy protective group; and each of $R^{4a}$, $R^{4b}$, and $R^{4c}$ is a hydrogen atom.

[13] A compound represented by Formula (7a),

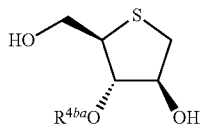
(7a)

(in the formula, $R^{4ba}$ is a p-toluoyl group).

[14] A method for manufacturing a compound represented by Formula (7b),

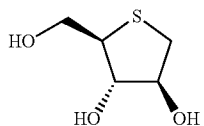
(7b)

obtaining a compound represented by Formula (12) by reacting a compound represented by Formula (10) with a compound represented by Formula (11).

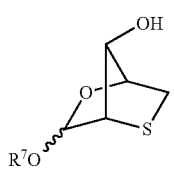
(10)

(in the formula, $R^7$ is a $C_{1-3}$ alkyl group which may be substituted), $R^{4ba}$-$L^1$ (11)

(in the formula, $L^1$ is a leaving group; and $R^{4ba}$ has the same definition as described above), and

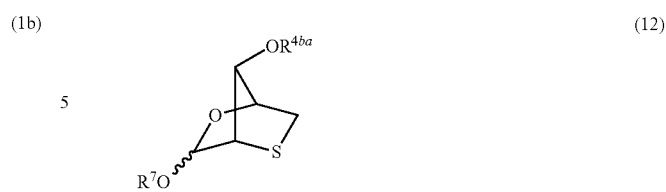
(12)

(in the formula, each of $R^{4ba}$ and $R^7$ has the same definition as described above);

then obtaining a compound represented by Formula (7a) by reacting the compound represented by Formula (12) with an acid and then subjecting the resulting compound to a reduction reaction,

(7a)

(in the formula, $R^{4ba}$ has the same definition as described above); and then subjecting the compound represented by Formula (7a) to a deprotection reaction.

[15] A method for manufacturing a compound represented by Formula (7b), comprising:

(7b)

obtaining a compound represented by Formula (15) by reacting a compound represented by Formula (13) with a compound represented by Formula (14),

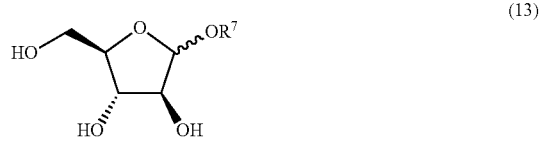
(13)

(in the formula, $R^7$ has the same definition as described above), $R^8$-$L^2$ (14)

(in the formula, $R^8$ is a $C_{1-3}$ alkylsulfonyl group which may be substituted or an arylsulfonyl group which may be substituted; and $L^2$ is a leaving group), and

(15)

(in the formula, each of $R^7$ and $R^8$ has the same definition as described above);

then obtaining a compound represented by Formula (17) by reacting the compound represented by Formula (15) with a compound represented by Formula (16)

 (16)

(in the formula, $R^9$ is an acyl group which may be substituted), and

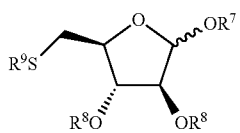 (17)

(in the formula, each of $R^7$, $R^8$, and $R^9$ has the same definition as described above);
then obtaining a compound represented by Formula (18) by reacting the compound represented by Formula (17) with a base,

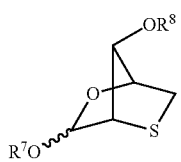 (18)

(in the formula, each of $R^7$ and $R^8$ has the same definition as described above);
then obtaining a compound represented by Formula (10) by subjecting the compound represented by Formula (18) to a deprotection reaction,

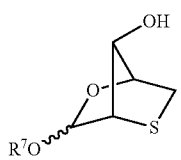 (10)

(in the formula, $R^7$ has the same definition as described above);
then obtaining a compound represented by Formula, (12) by reacting the compound represented by Formula (10) with a compound represented by Formula (11),

 (11)

(in the formula, each of $R^{4ba}$ and $L^1$ has the same definition as described above), and

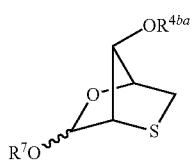 (12)

(in the formula, each of $R^{4ba}$ and $R^7$ has the same definition as described above);

then obtaining a compound represented by Formula (7a) by reacting the compound represented by Formula (12) with an acid and then subjecting the resulting compound to a reduction reaction,

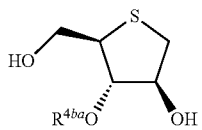 (7a)

(in the formula, $R^{4ba}$ has the same definition as described above); and then
subjecting the compound represented by Formula (7a) to a deprotection reaction.

[16] A method for protecting a 1,2-diol group or a 1,3-diol group, comprising reacting a 1,2-diol group or a 1,3-diol group with a group represented by Formula (19) in the presence of a base,

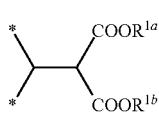 (19)

(in the formula, each of $R^{1a}$, $R^{1b}$ and * has the same definition as described above).

[17] A method for protecting a 1,2-diol group or a 1,3-diol group, comprising manufacturing a compound represented by Formula (21) by reacting a 1,2-diol group or a 1,3-diol group of a compound represented by Formula (20) with a compound represented by Formula (9) In the presence of a base,

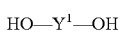 (20)

(in the formula, $Y^1$ is a $C_{2-3}$ alkylene group which may be substituted),

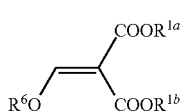 (9)

(in the formula, each of $R^{1a}$, $R^{1b}$, and $R^6$ has the same definition as described above), and

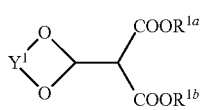 (21)

(in the formula, each of $R^{1a}$, $R^{1b}$, and $R^6$ has the same definition as described above).

[18] A protective agent for a 1,2-diol group or a 1,3-diol group, comprising a compound represented by Formula (9),

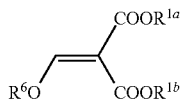

(9)

(in the formula, each of $R^{1a}$, $R^{1b}$, and $R^6$ has the same definition as described above).

[19] A method for deprotecting a protected 1,2-diol group or 1,3-diol group, comprising reacting a 1,2-diol group or a 1,3-diol group protected with a group represented by Formula (19) with a base,

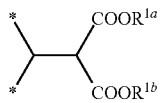

(19)

(in the formula, each of $R^{1a}$, $R^{1b}$, and * has the same definition as described above).

[20] A method for deprotecting a protected 1,2-diol group or 1,3-diol group, comprising manufacturing a compound represented by Formula (20) by reacting a compound which is represented by Formula (21) and has a protected 1,2-diol group or a protected 1,3-diol group with a base,

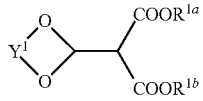

(21)

(in the formula, each of $R^{1a}$, $R^{1b}$, and $Y^1$ has the same definition as described above), and

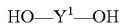

(20)

(in the formula, $Y^1$ has the same definition as described above).

The compound of the present invention is useful as an intermediate for manufacturing salacinol. The manufacturing method of the present invention is useful as a method for manufacturing salacinol. Furthermore, the protective group for a diol group of the present invention is a novel protective group, and the protective group and the methods of the present invention are useful as a protective group for a diol group and as methods for protecting and deprotecting a diol group.

DESCRIPTION OF THE PREFERRED EMBODIMENTS

Hereinafter, the present invention will be specifically described.

In the present invention, unless otherwise specified, % means mass percentage.

In the present invention, unless otherwise specified, each term has the following meaning.

A halogen atom means a fluorine atom, a chlorine atom, a bromine atom or an iodine atom.

A $C_{1-3}$ alkyl group means a methyl, ethyl, propyl, or isopropyl group.

A $C_{1-6}$ alkyl group means a linear or branched $C_{1-6}$ alkyl group such as methyl, ethyl, propyl, isopropyl, butyl, sec-butyl, isobutyl, tert-butyl, pentyl, and hexyl groups.

A $C_{2-6}$ alkenyl group means a linear or branched $C_{2-6}$ alkenyl group such as vinyl, allyl, propenyl, isopropenyl, butenyl, isobutenyl, 1,3-butadienyl, pentenyl, and hexenyl groups.

A $C_{2-3}$ alkylene group means an ethylene or propylene group or the like.

An aryl group means a phenyl or naphthyl group or the like.

An ar-$C_{1-6}$, alkyl group means benzyl, diphenylmethyl, trytyl, phenethyl, and naphthylmethyl groups or the like.

A $C_{1-6}$ alkoxy group means a linear or branched $C_{1-6}$ alkoxy group such as methoxy, ethoxy, propoxy, isopropoxy, butoxy, isobutoxy, sec-butoxy, tert-butoxy, pentyloxy, and hexyloxy groups.

A $C_{1-6}$ alkoxy $C_{1-6}$ alkyl group means methoxymethyl and 1-ethoxyethyl groups or the like.

A $C_{2-6}$ alkanoyl group means a linear or branched $C_{2-6}$ alkanoyl group such as acetyl, propionyl, valeryl, isovaleryl, and pivalolyl groups.

An aroyl group means a benzoyl or naphthyl group, or the like.

An acyl group means a formyl group, a $C_{2-6}$ alkanoyl group, an aroyl group, or the like.

A $C_{1-6}$ alkoxycarbonyl group means a linear or branched $C_{1-6}$ alkoxycarbonyl group such as methoxycarbonyl, ethoxycarbonyl, isopropoxycarbonyl, tert-butoxycarbonyl, and 1,1-dimethylpropoxycarbonyl groups.

An aryloxycarbonyl group means a phenyloxycarbonyl or naphthyloxycarbonyl group or the like.

A $C_{1-6}$ alkylamino group means a linear or branched $C_{1-6}$ alkylamino group such as methylamino, ethylamino, propylamino, isopropylamino, butylamino, sec-butylamino, tert-butylamino, pentylamino, and hexyl amino groups.

A di($C_{1-6}$ alkyl)amino group means a linear or branched di($C_{1-6}$)amino group such as dimethylamino, diethylamino, dipropylamino, diisopropylamino, dibutylamino, di(tert-butyl)amino, dipentylamino, dihexylamino, (ethyl)(methyl) amino, and (methyl)(propyl)amino groups.

A $C_{1-6}$ alkylthio group means methylthio, ethylthio, propylthio groups or the like.

A $C_{1-3}$ alkylsulfonyl group means methylsulfonyl and ethylsulfonyl groups or the like.

A $C_{1-6}$ alkylsulfonyl group means methylsulfonyl, ethylsulfonyl, and propynylsulfonyl groups or the like.

An arylsulfonyl group means a benzenesulfonyl, p-toluenesulfonyl, or naphthalenesulfonyl group or the like.

A $C_{1-6}$ alkylsulfonyloxy group means methylsulfonyloxy, ethylsulfonyloxy, and propylsulfonyloxy groups or the like.

An arylsulfonyloxy group means a benenesulfonyloxy, p-toluenesulfonyloxy or naphthalenesulfonyloxy group or the like.

A monocyclic nitrogen-containing heterocyclic group means azetidinyl, pyrrolidinyl, pyrrolinyl, pyrrolyl, piperidyl, tetrahydropyridyl, pyridyl, homopiperidinyl, octahydroazocinyl, pyrazolyl, piperazinyl, pyrazinyl, pyridazinyl, pyrimidinyl, homopiperazinyl, triazolyl, and tetrazolyl groups or the like that contain only a nitrogen atom as a heteroatom forming a ring.

A monocyclic oxygen-containing heterocyclic group means a tetrahydrofuranyl, furanyl, tetrahydropyranyl, or pyranyl group or the like.

A monocyclic sulfur-containing heterocyclic group means a thienyl group or the like.

A monocyclic nitrogen-oxygen-containing heterocyclic group means oxazolyl, isozaxolyl, oxadiazolyl, and morpholinyl groups or the like that contain only a nitrogen atom and an oxygen atom as heteroatoms forming a ring.

A monocyclic nitrogen-sulfur-containing heterocyclic group means thiazolyl, isothiazolyl, thiadiazolyl, thiomorpholinyl, 1-oxidothiomorpholinyl, and 1,1-dioxidothiomorpholinyl groups or the like that contain only a nitrogen atom and a sulfur atom as heteroatoms forming a ring.

A monocyclic heterocyclic group means a monocyclic nitrogen-containing heterocyclic group, a monocyclic oxygen-containing heterocyclic group, a monocyclic sulfur-containing heterocyclic group, a monocyclic nitrogen-oxygen-containing heterocyclic group, a monocyclic nitrogen-sulfur-containing heterocyclic group, or the like.

A bicyclic nitrogen-containing heterocyclic group means indolinyl, indolyl, isoindolinyl, isoindolyl, benzimidazolyl, indazolyl, benzotriazolyl, quinolyl, tetrahydroquinolinyl, tetrahydroisoquinolinyl, isoquinolinyl, quinolizinyl, cinnolinyl, phthalazinyl, quinazolinyl, dihydroquinoxalinyl, quinoxalinyl, naphthyridinly, purinyl, pteridinyl, and quinoclidinyl groups or the like that contain only a nitrogen atom as a heteroatom forming a ring.

A bicyclic oxygen-containing heterocyclic group means 2,3-dihydrobenzofuranyl, benzofuranyl, isobenzofuranyl, 1,3-benzodioxanyl, and 1,4-benzodioxanyl groups or the like that contain only an oxygen atom as a heteroatom forming a ring.

A bicyclic nitrogen-containing heterocyclic group means 2,3-dihydrobenzothienyl and enzothienyl groups or the like that contain only a sulfur atom as a heteroatom forming a ring.

A bicyclic nitrogen-oxygen-containing heterocyclic group means benzoxazolyl, benzisoxazolyl, benzoxadiazolyl, benzomorpholinyl, dihydropyranopyridyl, dihydrodioxinopyridyl, and dihydropyridooxazinyl groups or the like that contain only a nitrogen atom and an oxygen atom as heteroatoms forming a ring.

A bicyclic nitrogen-sulfur-containing heterocyclic group means benzothiazolyl, benzisothiazolyl, and benzothiadiazolyl groups or the like that contain only a nitrogen atom and a sulfur atom as heteroatoms forming a ring.

A bicyclic heterocyclic group means a bicyclic nitrogen-containing heterocyclic group, a bicyclic oxygen-containing heterocyclic group, a bicyclic sulfur-containing heterocyclic group, a bicyclic nitrogen-oxygen-containing heterocyclic group, a bicyclic nitrogen-sulfur-containing heterocyclic group, or the like.

A heterocyclic group means a monocyclic or bicyclic heterocyclic group.

A $C_{3-8}$ cycloalkyl ring means a cyclopropane, cyclobutane, cyclopentane, cyclohexane, cycloheptane, or cyclooctane ring.

A $C_{5-8}$ cycloalkyl ring means a cyclopentane, cyclohexane, cycloheptane, or cyclooctane ring.

A non-aromatic nitrogen-containing heterocyclic ring means azetidine, pyrrolidine, piperidine, homopiperidine, piperazine, and homopiperazine rings or the like that contain only a nitrogen atom as a heteroatom forming a ring.

A non-aromatic oxygen-containing heterocyclic ring means oxetane, tetrahydrofuran, tetrahydropyran, 1,3-dioxane, and 1,4-dioxane rings or the like that contain only an oxygen atom as a heteroatom forming a ring.

A non-aromatic sulfur-containing heterocyclic ring means a tetrahydrothiophene ring or the like.

A non-aromatic nitrogen oxygen-containing heterocyclic ring means morpholine and oxazepam rings or the like that contain only a nitrogen atom and a sulfur atom as heteroatoms forming a ring.

A non-aromatic nitrogen-sulfur-containing heterocyclic ring means a thiomorpholine ring or the like.

A non-aromatic heterocyclic ring means a non-aromatic nitrogen-containing heterocyclic ring, a non-aromatic oxygen-containing heterocyclic ring, a non-aromatic sulfur-containing heterocyclic ring, a non-aromatic nitrogen-oxygen-containing heterocyclic ring, or a non-aromatic nitrogen-sulfur-containing heterocyclic ring.

A silyl group means a trimethylsilyl, triethylsilyl, triisopropylsilyl, tributylsilyl, tert-butyldimethylsilyl, or tert-butyldiphenylsilyl group or the like.

A leaving group means a halogen atom, a $C_{1-6}$ alkylsulfonyloxy group, or an arylsulfonyloxy group. These groups may be substituted with one or more groups selected from a substituent group B.

A hydroxy protective group includes all the groups that can be used as general protective groups for a hydroxy group, and examples thereof include the groups described in W. Greene et al. Protective Groups in Organic Synthesis, $4^{th}$ edition, pp. 16-366, 2007, John Wiley & Sons, INC.

Specific examples thereof include a $C_{1-6}$ alkyl group, a $C_{2-6}$ alkenyl group, an ar-$C_{1-6}$ alkyl group, a $C_{1-6}$ alkoxy $C_{1-6}$ alkyl group, an acyl group, a $C_{1-6}$ alkoxycarbonyl group, a $C_{1-6}$ alkylsulfonyl group, an arylsulfonyl group, a tetrahydrofuranyl group, a tetrahydropyranyl group, a silyl group, and the like. These groups may be substituted with one or more groups selected from a substituent group A.

An amino protective group includes all of the groups that can be used as general protective groups for an amino group, and examples thereof include the groups described in W. Greene et al, Protective Groups in Organic Synthesis, $4^{th}$ edition, pp. 696-926, 2007, John Wiley & Sons, INC.

Specific examples thereof include an ar-$C_{1-6}$ alkyl group, a alkoxy $C_{1-6}$ alkyl group, a $C_{1-6}$ alkoxycarbonyl group, an aryloxycarbonyl group, a $C_{1-6}$ alkylsulfonyl group, an arylsulfonyl group, a silyl group, and the like. These groups may be substituted with one or more groups selected from a substituent group A.

A carboxy protective group includes all of the groups that can be used as general protective groups for a carboxy group, and examples thereof include W. Greene et al, Protective Groups in Organic Synthesis, $4^{th}$ edition, pp. 533-646, 2007, John Wiley & Sons, INC.

Specific examples thereof include a $C_{1-6}$ alkyl group, a $C_{2-6}$ alkenyl group, an aryl group, an ar-$C_{1-6}$ alkyl group, a $C_{1-6}$ alkoxy $C_{1-6}$ alkyl group, a silyl group, and the like. These groups may be substituted with one or more groups selected from a substituent group A.

In the present specification, each substituent group means the following.

Substituent group A: a halogen atom, a cyano group, a nitro group, an amino group which may be protected, a hydroxy group which may be protected, a carboxy group which may be protected, a $C_{1-6}$ alkyl group which may be substituted with one or more groups selected from a substituent group B, an aryl group which may be substituted with one or more groups selected from a substituent group B, a $C_{1-6}$ alkoxy group which may be substituted with one or more groups selected from a substituent group B, a $C_{1-6}$ alkylamino group which may be substituted with one or more groups selected from a substituent group B, a di($C_{1-6}$ alkyl)amino group which may be substituted with one or more groups selected from a substituent group B, and a $C_{1-6}$ alkylthio group which may be substituted with one or more groups selected from a substituent group B.

Substituent group B: a halogen atom, a cyano group, a nitro group, a $C_{1-6}$ alkyl group which may be substituted with a halogen atom, an aryl group which may be substituted with a halogen atom, and a $C_{1-6}$ alkoxy group which may be substituted with a halogen atom.

Examples of aliphatic hydrocarbons include pentane, hexane, cyclohexane, and the like.

Examples of halogenated hydrocarbons include methylene chloride, chloride, chloroform, 1,2-dichloroethane, and the like.

Examples of alcohols include methanol, ethanol, propanol, 2-propanol, butanol, 2-methyl-2-propanol, and the like.

Examples of ethers include diethyl ether, diisopropylether, dioxane, tetrahydrofuran, anisole, ethylene glycol dimethyl ether, diethylene glycol dimethyl ether, diethylene glycol diethyl ether, and the like.

Examples of esters include methyl acetate, ethyl acetate, propyl acetate, isopropyl acetate, butyl acetate, and the like.

Examples of ketones include acetone, 2-butanone, 4-methyl-2-pentanone, and the like.

Examples of nitriles include acetonitrile and the like.

Examples of amides include N,N-dimethylformamide, N,N-dimethylacetamide, N-methylpyrrolidone, and the like.

Examples of sulfoxides include dimethylsulfoxide and the like.

Examples of aromatic hydrocarbons include benzene, toluene, xylene, and the like.

Examples of ureas include 1,3-dimethyl-2-imidazolidinone and the like.

An inorganic acid means hydrochloric acid, hydrobromic acid, nitric acid, phosphoric acid, sulfuric acid, boric acid, hydrofluoric acid, or the like.

An organic acid means formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluene sulfonic acid, camphorsulfonic acid, or the like.

An acid means an inorganic acid or an organic acid.

An inorganic base means sodium hydroxide, potassium hydroxide, sodium hydrogen carbonate, sodium carbonate, potassium carbonate, cesium carbonate, tripotassium phosphate, tert-butoxypotassium, sodium ethoxide, sodium methoxide, sodium hydride, or the like.

An organic base means propylamine, dimethylamine, dibutylamine, triethylamine, diisopropylethylamine, pyridine, 2,6-lutidine, 4-dimethylaminopyridine, tetraethylammonium hydroxide, diazabicycloundecene, diazabicyclononene, guanidine, N-methylimidazole, morpholine, N-methylmorpholine, or the like.

A base means an inorganic base or an organic base.

The aryl group represented by $R^5$ may be substituted with one or more groups selected from the substituent group A.

The $C_{1-6}$ alkyl group represented by $R^6$ may be substituted with one or more groups selected from the substituent group A.

The $C_{1-3}$ alkyl group represented by $R^7$ may be substituted with one or more groups selected from the substituent group A.

Each of the $C_{1-3}$ to alkylsulfonyl group and the arylsulfonyl group represented by $R^8$ may be substituted with one or more groups selected from the substituent group A.

The acyl group represented by $R^9$ may be substituted with one or more groups selected from the substituent group A.

The $C_{2-3}$ alkylene group represented by $Y^1$ may be substituted with one or more groups selected from the substituent A.

Preferred examples of the compound represented by Formula (1) include the following compounds.

The compound represented by Formula (1) is preferably a compound in which each of $R^{1a}$ and $R^{1b}$ is a carboxy protective group.

The carboxy protective group represented by $R^{1a}$ and $R^{1b}$ is preferably a $C_{1-6}$ alkyl group which may be substituted with one or more groups selected from the substituent group A, a $C_{2-6}$ alkenyl group which may be substituted with one or more groups selected from the substituent group A, an aryl group which may be substituted with one or more groups selected from the substituent group A, an ar-$C_{1-6}$ alkyl group which may be substituted with one or more groups selected from the substituent group A, a $C_{1-6}$ alkyl group which may be substituted with one or more groups selected from the substituent group A, or a silyl group which may be substituted with one or more groups selected from the substituent group A, more preferably a $C_{1-6}$ alkyl group which may be substituted with one or more groups selected from the substituent group A, even more preferably a $C_{1-6}$ alkyl group, and particularly preferably a $C_{1-3}$ alkyl group.

The compound represented by Formula (1) is preferably a compound in which each of $R^2$ and $R^3$ is a hydroxy group.

The compound represented by Formula (1) is preferably a compound in which $R^2$ is a group represented by Formula (2), and $R^3$ is a group represented by Formula (3).

$$R^{4b}O\cdots\underset{R^{4c}O}{\overset{\overset{\displaystyle R^{4a}O}{\diagup}}{\bigcirc}}\!\!-\!\!S^+\!-\!\!* \qquad (2)$$

(In the formula, each of $R^{4a}$, $R^{4b}$, $R^{4c}$, and * has the same definition as described above.)

$$\text{-O}-\underset{\underset{O}{\|}}{\overset{\overset{O}{\|}}{S}}-\text{O}-* \qquad (3)$$

(in the formula, * has the same definition as described above.)

The compound represented by Formula (1) is preferably a compound in which each of $R^{4a}$, $R^{4b}$, and $R^{4c}$ is a hydrogen atom, a $C_{1-6}$ alkyl group which may be substituted with one or more groups selected from the substituent group A, a $C_{2-6}$ alkenyl group which may be substituted with one or more groups selected from the substituent group A, an ar-$C_{1-6}$ alkyl group which may be substituted with one or more groups selected from the substituent group A, a $C_{1-6}$ alkoxy $C_{1-6}$ alkyl group which may be substituted with one or more groups selected from the substituent group A, an acyl group which may be substituted with one or more groups selected from the substituent group A, a $C_{1-6}$ alkoxycarbonyl group which may be substituted with one or more groups selected from the substituent group A, a $C_{1-6}$ alkylsulfonyl group which may be substituted with one or more groups selected from the substituent group A, an arylsulfonyl group which may be substituted with one or more groups selected from the substituent group A, a tetrahydrofuranyl group, a tetrahydropyranyl group, or a silyl group which may be substituted with one or more groups selected from the substituent group A, more preferably a compound in which each of $R^{4a}$, $R^{4b}$, and $R^{4c}$ is a hydrogen atom, a $C_{1-6}$ alkyl group which may be substituted with one or more groups selected from the substituent group A, or an acyl group which may be substituted with one or more groups selected from the substituent group A, even more preferably a compound in which each of $R^{4a}$, $R^{4b}$, and $R^{4c}$ is a hydrogen atom or an acyl group, and particularly preferably a compound in which each of $R^{4a}$, $R^{4b}$, and $R^{4c}$ is a hydrogen atom.

The compound represented by Formula (1) is preferably a compound in which $R^2$ and $R^3$ are bonded to each other and represent a group represented by Formula (4).

  (4)

(In the formula, each of $X^1$ and * has the same definition as described above.)

The compound represented by Formula (1) is preferably a compound in which $R^5$ is an aryl group which may be substituted with one or more groups selected from the substituent group A, more preferably a compound in which $R^5$ is a phenyl group which may be substituted with one or more groups selected from the substituent group A, and even more preferably a compound in which $R^5$ is a phenyl group which may be substituted with one or more groups selected from the substituent group B.

Preferred examples of the manufacturing method of the present invention include the following manufacturing methods.

The manufacturing method of the present invention is preferably a manufacturing method using a compound in which each of $R^{1a}$ and $R^{1b}$ is a carboxy protective group.

The carboxy protective group represented by $R^{1a}$ and $R^{1b}$ is preferably a $C_{1-6}$ alkyl group which may be substituted with one or more groups selected from the substituent group A, a $C_{2-6}$ alkenyl group which may be substituted with one or more groups selected from the substituent group A, an aryl group which may be substituted with one or more groups selected from the substituent group A, an ar-$C_{1-6}$ alkyl group which may be substituted with one or more groups selected from the substituent group A, a $C_{1-6}$ alkoxy $C_{1-6}$ alkyl group which may be substituted with one or more groups selected from the substituent group A, or a silyl group which may be substituted with one or more groups selected from the substituent group A, more preferably a $C_{1-6}$ alkyl group which may be substituted with one or more groups selected from the substituent group A, even more preferably a $C_{1-6}$ alkyl group, and particularly preferably a $C_{1-3}$ alkyl group.

The manufacturing method of the present invention is preferably a manufacturing method using a compound in which each of $R^{4a}$, $R^{4b}$, and $R^{4c}$ is a hydrogen atom, a $C_{1-6}$ alkyl group which may be substituted with one or more groups selected from the substituent group A, a $C_{2-6}$ alkenyl group which may be substituted with one or more groups selected from the substituent group A, an ar-$C_{1-6}$ alkyl group which may be substituted with one or more groups selected from the substituent group A, a $C_{1-6}$ alkoxy $C_{1-6}$ alkyl group which may be substituted with one or more groups selected from the substituent group A, an acyl group which may be substituted with one or more groups selected from the substituent group A, a $C_{1-6}$ alkoxycarbonyl group which may be substituted with one or more groups selected from the substituent group A, a $C_{1-6}$ alkylsulfonyl group which may be substituted with one or more groups selected from the substituent group A, an arylsulfonyl group which may be substituted with one or more groups selected from the substituent group A, a tetrahydrofuranyl group, a tetrahydropyranyl group, or a silyl group which may be substituted with one or more groups selected from the substituent group A, more preferably a manufacturing method using a compound in which each of $R^{4a}$, $R^{4b}$, and $R^{4c}$ is a hydrogen atom, a $C_{1-6}$ alkyl group which may be substituted with one or more groups selected from the substituent group A, or an acyl group which may be substituted with one or more groups selected from the substituent group A, even more preferably a manufacturing method using a compound in which each of $R^{4a}$, $R^{4b}$, and $R^{4c}$ is a hydrogen atom or an acyl group, and particularly preferably a manufacturing method using a compound in which each of $R^{4a}$, $R^{4b}$, and $R^{4c}$ is a hydrogen atom.

The manufacturing method of the present invention is preferably a manufacturing method using a compound in which $R^5$ is an aryl group which may be substituted with one or more groups selected from the substituent group A, more preferably a manufacturing method using a compound in which $R^5$ is a phenyl group which may be substituted with one or more groups selected from the substituent group A, and even more preferably a manufacturing method using a compound in which $R^5$ is a phenyl group which may be substituted with one or more groups selected from the substituent group B.

The manufacturing method of the present invention is preferably a manufacturing method using a compound in which $R^6$ is a $C_{1-6}$ alkyl group which may be substituted with one or more groups selected from the substituent group A, more preferably a manufacturing method using a compound in which $R^6$ is a $C_{1-6}$ alkyl group which may be substituted with one or more groups selected from the substituent group B, even more preferably a manufacturing method using a compound in which $R^6$ is a $C_{1-6}$ alkyl group, and still more preferably a manufacturing method using a compound in which $R^6$ is a $C_{1-3}$ group.

The manufacturing method of the present invention is preferably a manufacturing method using a compound in which $R^7$ is a $C_{1-3}$ alkyl group which may be substituted with one or more groups selected from the substituent group A, more preferably a manufacturing method using a compound in which $R^7$ is a $C_{1-3}$ alkyl group which may be substituted with one of more groups selected from the substituent group B, and even more preferably a manufacturing method using a compound in which $R^7$ is a $C_{1-3}$ alkyl group.

The manufacturing method of the present invention is preferably a manufacturing method using a compound in which $R^8$ is a $C_{1-3}$ alkylsulfonyl group which may be substituted with one or more groups selected from the substituent group A or an arylsulfonyl group which may be substituted with one or more groups selected from the substituent group A, more preferably a manufacturing method using a compound in which $R^8$ is a $C_{1-3}$ alkylsulfonyl group which may be substituted with one or more groups selected from the substituent group B or an arylsulfonyl group which may be substituted with one or more groups selected from the substituent group B, and even more preferably a manufacturing method using a compound in which R⁸ is an arylsulfonyl group which may be substituted with one or more groups selected from the substituent group B.

The manufacturing method of the present invention is preferably a manufacturing method using a compound in which R⁹ is an acyl group which may be substituted with one or more groups selected, from the substituent group A, more preferably a manufacturing method using a compound in which R⁹ is a alkanoyl group which may be substituted with one or more groups selected from the substituent group B, and even more preferably a manufacturing method using a compound in which R⁹ is a $C_{2-6}$ alkanoyl group.

Next, the manufacturing method of the present invention will be described.

Manufacturing Method 1

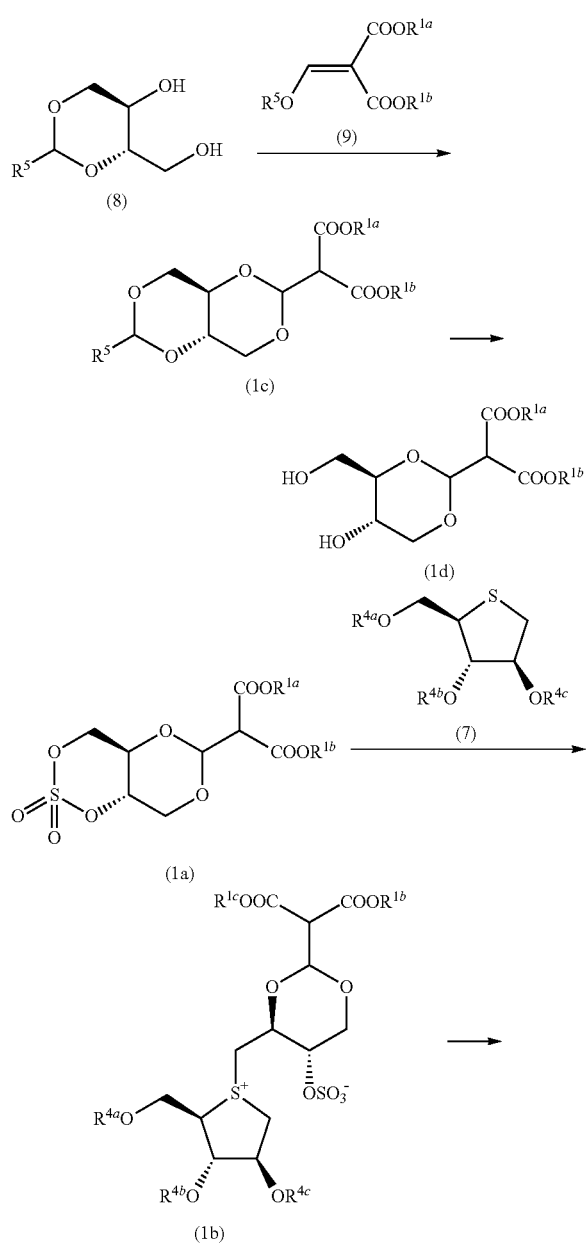

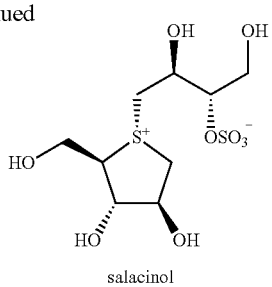

salacinol (In the formulae, each of $R^{1a}$, $R^{1b}$, $R^{4a}$, $R^{4b}$, $R^{4c}$, $R^5$, and $R^6$ has the same definition as described above.)

(1-1)

As the compound represented by Formula (9), for example, dimethyl methoxymethylene malonate is known.

The compound represented by Formula (1c) can be manufactured by reacting the compound represented by Formula (8) with the compound represented by Formula (9) in the presence of a base.

The solvent used in this reaction is not particularly limited as long as the solvent does not affect the reaction. Examples of the solvent include aliphatic hydrocarbons, halogenated hydrocarbons, ethers, esters, ketones, nitriles, amides, sulfoxides, and aromatic hydrocarbons. These solvents may be used by being mixed together.

Examples of preferred solvents include ethers, esters, ketones, nitriles, and amides, and among these, ethers are more preferable.

The amount of the solvent used is not particularly limited. The amount of the solvent used may be 1 time to 50 times (v/w) as much as the amount of the compound represented by Formula (8), and preferably 1 time to 15 times (v/w) as much as the amount of the compound.

Examples of the base used in the reaction include inorganic bases, and among these, tert-butoxypotassium, sodium ethoxide, and sodium methoxide are preferable, and tert-butoxypotassium is more preferable.

The amount of the base used is 0.01 times to 5 times as much as the amount of the compound represented by (8) in terms of mole, preferably 0.02 times to 2 times as much as the amount of the compound in terms of mole, and more preferably 0.03 times to 1 time as much as the amount of the compound in terms of mole.

The amount of the compound represented by Formula (9) used is 1.0 time to 2.0 times as much as the amount of the compound represented by formula (8) in terms of mole, preferably 1.0 time to 1.5 times as much as the compound in terms of mole, and more preferably 1.0 time to 1.2 times as much as amount of the amount of the compound in terms of mole.

The reaction temperature may be −20° C. to 100° C., preferably −10° C. to 80° C., and even more preferably −5° C. to 60° C.

The reaction time may be 5 minutes to 50 hours, preferably 5 minutes to 24 hours, and even more preferably 5 minutes to 6 hours.

(1-2)

The compound represented by Formula (1d) can be manufactured by subjecting the compound represented by formula (1c) to a deprotection reaction.

Examples of the deprotection reaction include the method described in W. Greene et al, Protective Groups in Organic Synthesis, 4$^{th}$ edition, pp. 299-366, 2007, John Wiley & Sons, INC, and the like.

Specifically, examples of the deprotection reaction include a hydrogenation reaction using a catalyst, a hydrolysis reaction using an acid, and the like.

The solvent used in the hydrogenation reaction is not particularly limited as long as the solvent does not affect the reaction. Examples of the solvent include aliphatic hydrocarbons, halogenated hydrocarbons, alcohols, ethers, esters, ketones, nitriles, amides, sulfoxides, aromatic hydrocarbons, ureas, and water. These solvents may be used by being mixed together.

Preferred examples of the solvent include alcohols, ethers, esters, ketones, nitriles, and amides. Among these, alcohols and esters are more preferable.

The amount of the solvent used is not particularly limited. The amount of the solvent used may be 1 time to 50 times (v/w) as much as the amount of the compound represented by Formula (1c), and preferably 1 time to 15 times (v/w) as much as the amount of the compound.

Examples of the catalyst used in this reaction include ruthenium, rhodium, palladium, platinum, and nickel catalysts. Among these, Raney nickel, palladium-carbon (Pd/C), rhodium-carbon (Rh/C), an Adam's catalyst (PtO$_2$), and a Pearlman's catalyst (Pd(OH)$_2$) are preferable, and palladium-carbon and a Pearlman's catalyst are more preferable.

The amount of the catalyst used is 0.001% to 10% of the amount of the compound represented by Formula (1c), and preferably 0.01% to 0.2% of the amount of the compound, and more preferably 0.05% to 0.1% of the amount of the compound.

The reaction temperature may be −20° C. to 100° C., preferably −10° C. to 80° C., and more preferably −5° C. to 60° C.

The reaction time may be 5 minutes to 50 hours, preferably 5 minutes to 24 hours, and more preferably 5 minutes to 6 hours.

The solvent used in the hydrolysis reaction is not particularly limited as long as the solvent does not affect the reaction. Examples of the solvent include halogenated hydrocarbons, alcohols, ethers, ketones, nitriles, amides, sulfoxides, and water. These solvents may be used by being mixed together.

Preferred examples of the solvent include alcohols, ethers, nitriles, and water, and among these, alcohols are more preferable.

The amount of the solvent used is not particularly limited. The amount of the solvent used may be 1 time to 50 times (v/w) as much as the amount of the compound represented by Formula (1c), and more preferably 1 time to 15 times (v/w) as much as the amount of the compound.

Examples of the acid used in this reaction include inorganic acids and organic adds. Among these, hydrochloric acid, sulfuric acid, trifluoroacetic acid, and p-toluenesulfonic acid are preferable.

The amount of the acid used is 0.001 times to 2 times as much as the amount of the compound represented by Formula (1c) in terms of mole, preferably 0.005 times to 1.5 times as much as the amount of the compound in terms of mole, and more preferably 0.01 times to 1 time as much as the amount of the compound in terms of mole.

The reaction temperature may be −20° C. to 100° C., preferably −10° C. to 80° C. and more preferably −5° C. to 60° C.

The reaction time may be 5 minutes to 50 hours, preferably 5 minutes to 24 hours, and more preferably 5 minutes to 6 hours.

By the method for protecting a 1,3-diol group of the compound represented by Formula (8) with the group represented by Formula (19)

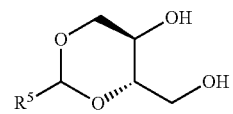

(8)

(in the formula, R$^5$ has the same definition as described above)

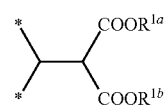

(19)

(in the formula, each of R$^{1a}$, R$^{1b}$, and * has the same definition as described above), it is possible to manufacture the compound represented by Formula (1c) without decomposing a protective group for a 1,3-diol group represented by Formula (A)

(A)

(in the formula, each of R$^5$ and * has the same definition as described above)

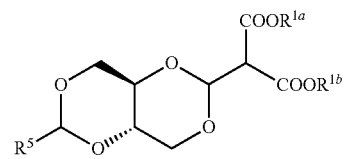

(1c)

(in the formula, each of R$^{1a}$, R$^{1b}$, and R$^5$ has the same definition as described above).

The protective group for a diol group represented by Formula (19) is stable in a step of deprotecting the protective group for a diol group represented by Formula (A) (for example, a hydrogenation reaction using a catalyst and a hydrolysis reaction performed in the presence of an acid).

The use of the group represented by Formula (19) as a protective group for a diol group makes it possible to selectively protect and deprotect diol groups even in a case where two or more diol groups are present in a molecule.

(1-3)

The compound represented by Formula (1a) can be manufactured by reacting the compound represented by Formula (1d) with a sulfur-containing compound in the presence of a base and subjecting the resulting compound to an oxidation reaction if necessary.

The solvent used is this reaction is not particularly limited as long as the solvent does not affect the reaction. Examples of the solvent include aliphatic hydrocarbons, halogenated hydrocarbons, ethers, nitriles, and aromatic hydrocarbons. These solvents may be used by being mixed together.

Preferred examples of the solvent include halogenated hydrocarbons, nitriles, and aromatic hydrocarbons, and among these, halogenated hydrocarbons are more preferable.

The amount of the solvent used is not particularly limited. The amount of the solvent used may be 1 time to 50 times (v/w) as much as the amount of the compound represented by formula (1c), and preferably 1 time to 15 times (v/w) as much as the amount of the compound.

Examples of the base used in this reaction include organic bases, and among these, triethylamine and diisopropylamine are preferable.

The amount of the base used is 0.8 times to 5 times as much as the amount of the compound represented by formula (1d) in terms of mole, preferably 1 time to 3 times as much as the amount of the compound in terms of mole, and more preferably 1.2 times to 2 times as much as the amount of the compound in terms of mole.

Examples of the sulfur-containing compound used in this reaction include sulfur dichloride, thionyl chloride, sulfuryl chloride, and sulfur trioxide, and among these, thionyl chloride is preferable.

The amount of the sulfur-containing compound used is 0.8 times to 5 times as much as the amount of the compound represented by Formula (1d) in terms of mole, preferably 0.9 times to 3 times as much as the amount of the compound in terms of mole, and more preferably 1 time to 2 times as much as the amount of the compound in terms of mole.

The reaction temperature may be <20° C. to 100° C., preferably −15° C. to 70° C., and even more preferably −10° C. to 40° C.

The reaction time may be 5 minutes to 50 hours, preferably 5 minutes to 24 hours, and even more preferably 5 minutes to 6 hours.

In a case where sulfur dichloride and thionyl chloride are used as the sulfur-containing compound, it is preferable to cause an oxidation reaction.

The solvent used in the oxidation reaction is not particularly limited as long as the solvent does not affect the reaction. Examples of the solvent include aliphatic hydrocarbons, halogenated hydrocarbons, ethers, nitriles, and aromatic hydrocarbons. These solvents may be used by being mixed together.

Preferred examples of the solvent include halogenated hydrocarbons, nitriles, and aromatic hydrocarbons, and among these, halogenated hydrocarbons and nitriles are more preferable.

The oxidant used in the oxidation reaction is not particularly limited. The oxidant is preferably potassium permanganate, ruthenium tetroxide, ruthenium (III) chloride-sodium periodate, or the like.

The amount of the oxidant used is 0.005 times to 0.2 times as much as the amount of the compound represented by Formula (1d) in terms of mole, preferably 0.01 times to 0.1 times as much as the amount of the compound in terms of mole, and more preferably 0.02 times to 0.05 times as much as the amount of the compound in terms of mole.

The reaction temperature may be −20° C. to 100° C., preferably −10° C. to 80° C., and more preferably −5° C. to 60° C.

The reaction time may be 5 minutes to 50 hours, preferably 5 minutes to 24 hours, and more preferably 5 minutes to 6 hours.

(1-4)

As the compound represented by Formula (7), for example, (2R,4S)-2-(hydroxymethyl)tetrahydrothiophene-3,4-diol is known.

The compound represented by Formula (1b) can be manufactured by reacting the compound represented by Formula (1a) with the compound represented by Formula (7) in the presence of a base.

The solvent used in this reaction is not particularly limited as long as the solvent does not affect the reaction. Examples of the solvent include aliphatic hydrocarbons, halogenated hydrocarbons, alcohols, ethers, esters, ketones, nitriles, amides, sulfoxides, aromatic hydrocarbons, ureas, and water. These solvents may be used by being mixed together.

Preferred examples of the solvent include alcohols, ethers, ketones, nitriles, and sulfoxides, and among these, ketones are more preferable.

The amount of the solvent used is not particularly limited. The amount of the solvent used may be 1 time to 50 times (v/w) as much as the amount of the compound represented by Formula (1a), and preferably 1 time to 15 times (v/w) as much as the amount of the compound.

Examples of the base used in this reaction include inorganic bases and organic bases. Among these, sodium, hydrogen carbonate, potassium carbonate, pyridine, 2,6-lutidine, and 4-dimethylaminopyridine are preferable, and 2,6-lutidine is more preferable.

The amount of the base used is 0.01 times to 5 times as much as the amount of the compound represented by Formula (1a) in terms of mole, preferably 0.02 times to 2 times as much as the amount of the compound in terms of mole, and more preferably 0.03 times to 1 time as much as the amount of the compound in terms of mole.

The amount of the compound represented by Formula (7) used is 0.5 times to 2 times as much as the amount of the compound represented by Formula (1a) in terms of mole, preferably 0.7 times to 1.2 times as much as the amount of the compound in terms of mole, and more preferably 0.8 times to 1.1 times as much as the amount of the compound in terms of mole.

The reaction temperature may be 0° C. to 150° C., preferably 10° C. to 100° C., and more preferably 25° C. to 80° C.

The reaction time may be 5 minutes to 72 hours, preferably 30 minutes to 50 hours, and more preferably 1 hour to 24 hours.

The compound represented by Formula (1b) contains isomers (a trans-isomer (1b-1) and a cis-isomer (1b-2)).

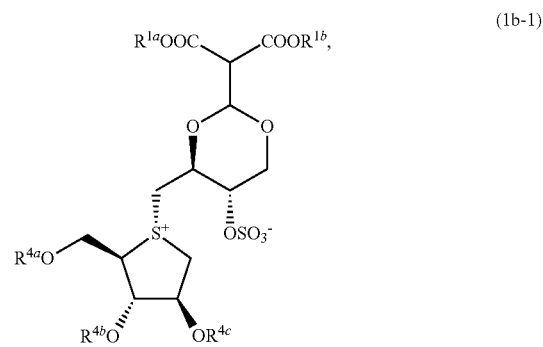

(1b-1)

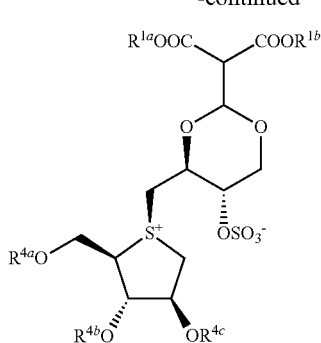

(1b-2)

The inventors of the present invention found that the compound represented by Formula (1b-2) can be converted into the compound represented by Formula (1b-1) through heating. Therefore, these isomers may be used in the next reaction after being isolated, but it is preferably to use these isomers as they are in the next reaction without isolating them.

(1-5)

Salacinol can be manufactured by subjecting the compound represented by Formula (1b) to a deprotection reaction in the presence of a base.

The solvent used in this reaction is not particularly limited as long as the solvent does not affect the reaction. Examples of the solvent include aliphatic hydrocarbons, halogenated hydrocarbons, alcohols, ethers, esters, ketones, nitriles, amides, sulfoxides, aromatic hydrocarbons, ureas, and water. These solvents may be used by being mixed together.

Preferred examples of the solvent include alcohols, ethers, esters, ketones, nitriles, and water, and among these, alcohols, ethers, esters, and water are more preferable.

The amount of the solvent used is not particularly limited. The amount of the solvent used may be 1 time to 50 times (v/w) as much as the amount of the compound represented by Formula (1b), and preferably 1 time to 15 times (v/w) as much as the amount of the compound.

Examples of the base used in this reaction include inorganic bases and organic bases. Among these, sodium hydrogen carbonate, sodium carbonate, potassium carbonate, sodium methoxide, propylamine, diethylamine, dibutylamine, triethylamine, diisopropylethylamine, pyridine, 2,6-lutidine, 4-dimethylaminopyridine, tetraethylammonium hydroxide, diazabicycloundecene, diazabicyclononene, guanidine, and morpholine are preferable, and sodium hydrogen carbonate, potassium carbonate, sodium methoxide, propylamine, diethylamine, dibutylamine, triethylamine, diisopropylethylamine, pyridine, and morpholine are more preferable.

The amount of the base used is 0.1 times to 5 times as much as the amount of the compound represented by Formula (1b) in terms of mole, preferably 0.5 times to 2 times as much as the amount of the compound in terms of mole, and more preferably 0.8 times to 1.5 times as much as the amount of the compound in terms of mole.

The reaction temperature may be 0° C. to 150° C., preferably 10° C. to 100° C., and more preferably 25° C. to 80° C.

The reaction times may be 5 minutes to 72 hours, preferably 30 minutes to 50 hours, and more preferably 1 hour to 24 hours.

The protective group for a diol group represented by Formula (19) is easily deprotected by a base. In contrast, a methylene group, an isopropylidene group (acetonide), a benzylidene group, and the like that are widely used as protective groups for a diol group are not easily deprotected by a base.

(19)

(In the formula, each of $R^{1a}$, $R^{1b}$, and * has the same definition as described above.)

The use of the group represented by Formula (19) as a protective group for a diol group makes it possible to selectively protect and deprotect diol groups even in a case where two or more diol groups are present in a molecule.

In a case where the reaction is performed, using the compound represented by Formula (1b-2), an isomer of salacinol is generated in some cases.

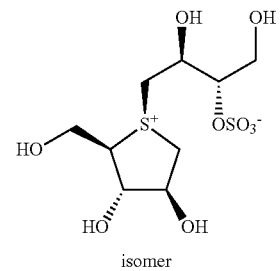

isomer

In this case, it is preferable that the isomer of salacinol is converted into salacinol by being subjected to a heating treatment as it is without being isolated.

Manufacturing Method 2

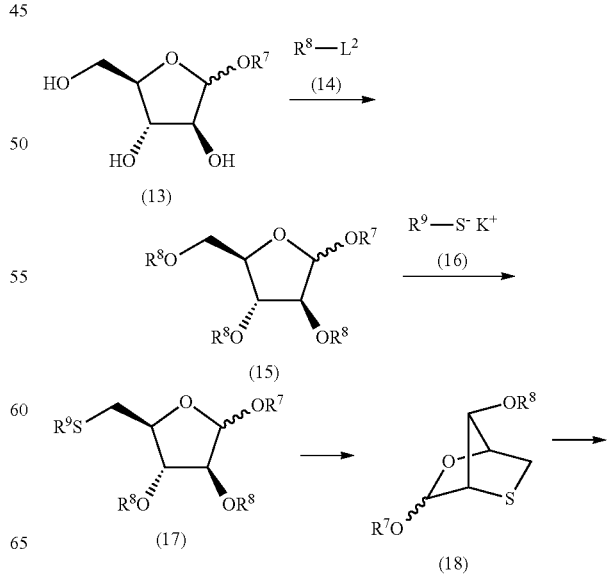

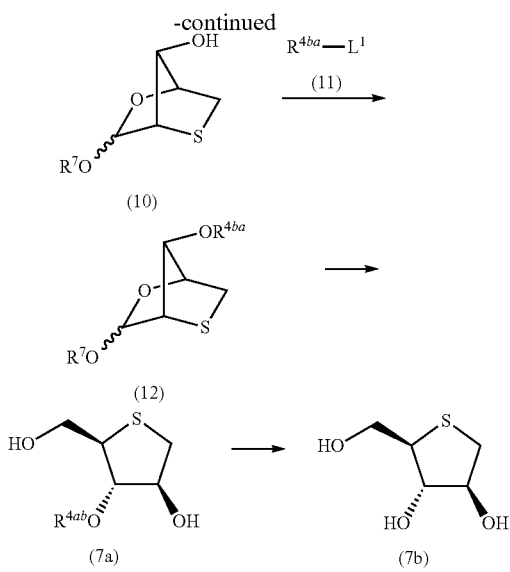

(In the formulae, each of $R^{4ba}$, $R^7$, $R^8$, $R^9$, $L^1$, and $L^2$ has the same definition as described above.)

(2-1)

As the compound represented by Formula (13), for example, (2R,3S,4S)-2-(hydroxymethyl)-5-methoxytetrahydrofuran-3,4-diol is known. The compound represented by Formula (13) may be prepared in a system.

As the compound represented by Formula (14), for example, p-toluenesulfonyl chloride is known.

The compound represented by Formula (15) can be manufactured by reacting the compound represented by Formula (13) with the compound represented by Formula (14) in the presence of a base.

The solvent used in this reaction is not particularly limited as long as the solvent does not affect the reaction. Examples of the solvent include a aliphatic hydrocarbons, halogenated hydrocarbons, ethers, ester, ketones, nitriles, amides, sulfoxides, aromatic hydrocarbons, ureas, and water. These solvents may be used by being mixed together.

Preferred examples of the solvent include ethers, esters, ketones, nitriles, and amides, and among these, nitriles are more preferable.

The amount of the solvent used is not particularly limited. The amount of the solvent used may be 1 time to 50 times (v/w) as much as the amount of the compound represented by Formula (13), and preferably 1 time to 15 times (v/w) as much as the amount of the compound.

Examples of the base used in this reaction include organic bases. Among these, triethylamine, diisopropylethylamine, pyridine, 4-dimethylaminopyridine, and N-methylimidazole are preferable.

The amount of the base used is 2.7 times to 10 times as much as the amount of the compound represented by Formula (13) in terms of mole, preferably 2.8 times to 6 times as much as the amount of the compound in terms of mole, and more preferably 2.9 times to 4 times as much as the amount of the compound in terms of mole.

The amount of the compound represented by Formula (14) used is 2.7 times to 10 times as much as the amount of the compound represented by Formula (13) in terms of mole, preferably 3 times to 6 times as much as the amount of the compound in terms of mole, and more preferably 3 times to 4 times as much as the amount of the compound in terms of mole.

The reaction temperature may be −10° C. to 60° C., preferably 0° C. to 50° C. and more preferably 10° C. to 40° C.

The reaction time may be 30 minutes to 24 hours, preferably 1 hour to 12 hours, and more preferably 1.5 hours to 8 hours.

(2-2)

As the compound represented by Formula (16), for example, S-potassium thioacetate is known.

The compound represented by Formula (17) can be manufactured by reacting the compound represented by Formula (15) with the compound represented by Formula (16).

The solvent used in this reaction is not particularly limited as long as the solvent does not affect the reaction. Examples of the solvent include aliphatic hydrocarbons, halogenated hydrocarbons, ethers, esters, ketones, nitriles, amides, sulfoxides, aromatic hydrocarbons, ureas, and water. These solvents may be used by being mixed together.

Preferred examples of the solvent include ethers, esters, ketones, nitriles, and amides, and among these, amides are more preferable.

The amount of the solvent used is not particularly limited. The amount of the solvent used may be 1 time to 50 times (v/w) as much as the amount of the compound represented by Formula (15), and preferably 1 time to 15 times (v/w) as much as the amount of the compound.

The amount of the compound represented by Formula (16) used is 0.8 times to 5 times as much as the amount of the compound represented by Formula (15) in terms of mole, preferably 0.9 times to 4 times as much as the amount of the compound in terms of mole, and more preferably 1 time to 3 times as much as the amount of the compound in terms of mole.

The reaction temperature may be 10° C. 200° C., preferably 20° C. to 150° C., and more preferably 30° C. to 100° C.

The reaction times may be 30 minutes to 24 hours, preferably 1 hour to 18 hours, and more preferably 1.5 hours to 12 hours.

(2-3)

The compound represented by Formula (18) can be manufactured by reacting the compound represented by Formula (17) with a base.

The solvent used in this reaction is not particularly limited as long as the solvent does not affect the reaction. Examples of the solvent include aliphatic hydrocarbons, halogenated hydrocarbons, alcohols, ethers, esters, ketones, nitriles, amides, sulfoxides, aromatic hydrocarbons, ureas, and water. These solvents may be used by being mixed together.

Preferred examples of the solvent include alcohols, ethers, esters, ketones, nitriles, amides, and sulfoxides, and among these, alcohols are more preferable.

The amount of the solvent used is not particularly limited. The amount of the solvent used may be 1 time to 50 times (v/w) as much as the amount of the compound represented by formula (17), and preferably 1 time to 15 times (v/w) as much as the amount of the compound.

Examples of the base used in this reaction include inorganic bases and organic bases. Among these, potassium, carbonate, tert-butoxypotassium, triethylamine, and pyridine are preferable.

The amount of the base used is 0.9 times to 5 times as much as the amount of the compound represented by Formula (17) in terms of mole, preferably 0.95 times to 3 times as much as the amount of the compound in terms of mole, and more preferably 1 time to 2 times as much as the amount of the compound in terms of mole.

The reaction temperature may be 10° C. to 200° C., preferably 20° C. to 150° C., and more preferably 30° C. to 100° C.

The reaction time may be 30 minutes to 12 hours, preferably 1 hour to 8 hours, and more preferably 1.5 hours to 4 hours.

The compound represented by Formula (18) may be used in the next reaction after being isolated. However, it is preferable to use the compound as it is in the next reaction without isolating it.

(2-4)

The compound represented by Formula (10) can be manufactured by subjecting the compound represented by Formula (18) to a deprotection reaction.

Examples of the deprotection reaction include the method described in W. Greene et al, Protective Groups in Organic Synthesis, 4$^{th}$ edition, pp. 272-279, 2007, John Wiley & Sons, INC., and the like.

Specifically examples of the deprotection reaction include a hydrolysis reaction using a base, and the like.

The solvent used in the hydrolysis reaction is not particularly limited as long as the solvent does not affect the reaction. Examples of the solvent include aliphatic hydrocarbons, halogenated hydrocarbons, ethers, esters, ketones, nitriles, amides, sulfoxides, aromatic hydrocarbons, ureas, and water. These solvents may be used by being mixed together.

Preferred examples of the solvent include alcohols, ethers, esters, ketones, nitriles, amides, sulfoxides, and water, and among these, mixed solvents of alcohols and water are more preferable.

The amount of the solvent used is not particularly limited. The amount of the solvent used may be 1 time to 50 times (v/w) as much as the amount of the compound represented by formula (18), and preferably 1 time to 15 times (v/w) as much as the amount of the compound.

Examples of the base used in the hydrolysis reaction include inorganic bases. Among these, sodium hydroxide and potassium hydroxide are preferable.

The amount of the base used is 1 time to 20 times as much as the amount of the compound represented by Formula (18) in terms of mole, preferably 1 time to 15 times as much as the amount of the compound in terms of mole, and more preferably 1 time to 10 times as much as the amount of the compound in terms of mole.

The reaction temperature may be 10° C. to 200° C., preferably 20° C. to 150° C., and more preferably 30° C. to 100° C.

The reaction time may be 10 minutes to 12 hours, preferably 20 minutes to 8 hours, and more preferably 30 minutes to 4 hours.

(2-5)

As the compound represented by Formula (11), for example, p-toluoyl chloride is known.

The compound represented by Formula (12) can be manufactured by reacting the compound represented by Formula (10) with the compound represented by Formula (11) in the presence of a base.

The solvent used in this reaction is not particularly limited as long as the solvent does not affect the reaction. Examples of the solvent include aliphatic hydrocarbons, halogenated hydrocarbons, ethers, esters, ketones, nitriles, amides, sulfoxides, aromatic hydrocarbons, ureas, and water. These solvents may be used by being mixed together.

Preferred examples of the solvent include ethers, esters, ketones, nitriles, amides, and aromatic hydrocarbons, and among these, esters and aromatic hydrocarbons are more preferable.

The amount of the solvent used is not particularly limited. The amount of the solvent used may be 1 time to 50 times (v/w) as much as the amount of the compound represented by Formula (10), and preferably 1 time to 15 times (v/w) as much as the amount of the compound.

Examples of the base used in this reaction include inorganic bases and organic bases. Among these, sodium hydroxide, potassium carbonate, sodium methoxide, triethylamine, and pyridine are preferable.

The amount of the base used is 1 time to 10 times as much as the amount of the compound represented by Formula (10) in terms of mole, preferably 1 time to 5 times as much as the amount of the compound in terms of mole, and more preferably 1 time to 3 times as much as the amount of the compound in terms of mole.

The amount of the compound represented by Formula (11) used is 0.9 times to 5 times as much as the amount of the compound represented by Formula (10) in terms of mole, preferably 0.95 times to 3 times as much as the amount of the compound in terms of mole, and more preferably 1 time to 2 times as much as the amount of the compound in terms of mole.

The reaction temperature may be −10° C. to 60° C., preferably 0° C. to 50° C., and more preferably 10° C. to 40° C.

The reaction time may be 30 minutes to 12 hours, preferably 1 hour to 8 hours, and more preferably 1.5 hours to 4 hours.

(2-6)

The compound represented by Formula (7a) can be manufactured by reacting the compound represented by Formula (12) with an acid and then subjecting the resulting compound to a reduction reaction.

The solvent used in this reaction is not particularly limited as long as the solvent does not affect the reaction. Examples of the solvent include aliphatic hydrocarbons, halogenated hydrocarbons, alcohol, ethers, esters, ketones, nitriles, amides, sulfoxides, aromatic hydrocarbons, ureas, and water. These solvents may be used by being mixed together.

Preferred examples of the solvent include alcohol, ether, and water, and among these, mixed solvents of ethers and water are more preferable.

The amount of the solvent used is not particularly limited. The amount of the solvent used may be 1 time to 50 times (v/w) as much as the amount of the compound represented by Formula (12), and preferably 1 time to 15 times (v/w) as much as the amount of the compound.

Examples of the acid used in this reaction include inorganic acids and organic acids. Among these, hydrochloric acid, sulfuric acid, p-toluenesulfonic acid, and camphorsulfonic acid are preferable.

The amount of the acid used is 1 time to 5 times as much as the amount of the compound represented by Formula (12) in terms of mole, preferably 1 time to 3 times as much as the amount of the compound in terms of mole, and more preferably 1 time to 2 times as much as the amount of the compound in terms of mole.

Examples of the reductone used in this reaction include complex hydride compounds such as lithium aluminum hydride, sodium triacetoxyborohydride, sodium cyanoborohydride, and sodium borohydride; borane; sodium; and sodium amalgam. It is also possible to use electrolytic reduction using copper or platinum as a cathode; contact reduction using Raney nickel, platinum oxide, or palladium black; reduction using "zinc-acid"; and the like.

Preferred examples of the reductone include sodium borohydride. A solid of sodium borohydride or a solution of sodium borohydride can be used.

The amount of the reductone used is 1 time to 5 times as much as the amount of the compound represented by Formula (12) in terms of mole, preferably 1 time to 4 times as much as the amount of the compound in terms of mole, and more preferably 1 time to 3 times as much as the amount of the compound in terms of more.

The temperature of the reaction with an acid may be 0° C. to 150° C., preferably 10° C. to 100° C., and more preferably 20° C. to 80° C.

The time of the reaction with an acid may be 10 minutes to 12 hours, preferably 20 minutes to 8 hours, and more preferably 30 minutes to 4 hours.

The temperature of the reduction reaction may be −10° C. to 60° C., preferably 10° C. to 50° C., and more preferably 10° C. to 40° C.

The time of the reduction reaction may be 10 minutes to 12 hours, preferably 20 minutes to 8 hours, and more preferably 30 minutes to 4 hours.

(2-7)

The compound represented by Formula (7b) can be manufactured by subjecting the compound represented by Formula (7a) to a deprotection reaction.

Examples of the deprotection reaction include the method described in W. Greene et al, Protective Groups in Organic Synthesis, 4$^{th}$ edition, pp. 255-205, 2007, John Wiley & Sons, INC., and the like.

Specifically, examples of the deprotection reaction include a hydrolysis reaction using a base.

The solvent used in the hydrolysis reaction is not particularly limited as long as the solvent does not affect the reaction. Examples of the solvent include aliphatic hydrocarbons, halogenated hydrocarbons, alcohols, ethers, esters, ketones, nitriles, amides, sulfoxides, aromatic hydrocarbons, ureas, and water. These solvents may be used by being mixed together.

Preferred examples of the solvent include alcohols, ethers, and water, and among these, alcohols are more preferable.

The amount of the solvent used is not particularly limited. The amount of the solvent used may be 1 to 50 times (v/w) as much as the amount of the compound represented by Formula (7a), and preferably 1 to 15 times (v/w) as much as the amount of the compound.

Examples of the base used in the hydrolysis reaction include inorganic bases and organic bases. Among these, sodium, hydroxide, potassium carbonate, and sodium methoxide are preferable.

The amount of the base used is 0.001 times to 3 times as much as the amount of the compound represented by Formula (7a) in terms of mole, preferably 0.005 times to 1 time as much as the amount of the compound in terms of mole, and more preferably 0.01 times to 0.5 times as much as the amount of the compound in terms of mole.

The reaction temperature may be −10° C. to 80° C., preferably 0° C. to 60° C., and more preferably 10° C. to 40° C.

The reaction time may be 10 minutes to 24 hours, preferably 20 minutes to 12 hours, and more preferably 30 minutes to 8 hours.

Manufacturing Method 3

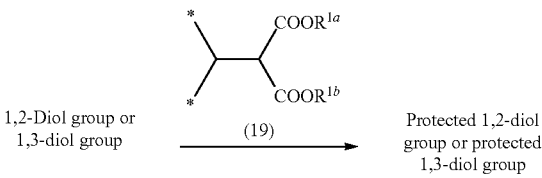

(In the formula, each of $R^{1a}$, $R^{1b}$, and * has the same definition as described above.)

A 1,2-diol group or a 1,3-diol group is reacted with the group represented by Formula (19) in the presence of a base, and in this way, the diol group can be protected.

Specifically, the compound represented by Formula (21) is manufactured by reacting the compound represented by Formula (20) with the compound represented by Formula (9) in the presence of a base, and in this way, a diol group can be protected. That is, the compound represented by Formula (9) is useful as a protective agent for a 1,2-diol group or a 1,3-diol group.

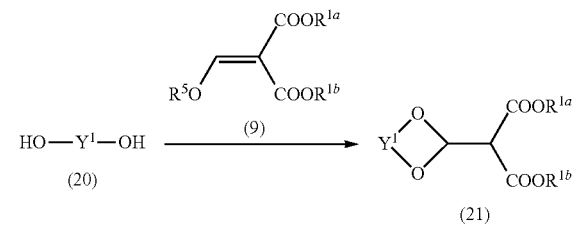

(In the formula, each of $R^{1a}$, $R^{1b}$, $R^6$, and $Y^1$ has the same definition as described above.)

The solvent used in this reaction is not particularly limited as long as the solvent does not affect the reaction. Examples of the solvent include aliphatic hydrocarbons, halogenated hydrocarbons, ethers, esters, ketones, nitriles, amides, sulfoxides, and aromatic hydrocarbons. These solvents may be used by being mixed together.

Preferred examples of the solvent include ethers, esters, ketones, nitriles, and amides, and among these, ethers are more preferable.

The amount of the solvent used is not particularly limited. The amount of the solvent used may be 1 time to 50 times (v/w) as much as the amount of the compound represented by Formula 20), and preferably 1 time to 15 times (v/w) as much as the amount of the compound.

The compound represented by Formula (20) that is used in this reaction is not particularly limited as long as the compound has a diol group in a molecule.

Specifically, the compound represented by Formula (20) can be represented by, for example, Formula (20a).

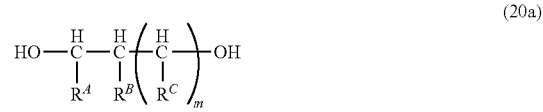

(In the formula, m is 0 or 1; $R^A$, $R^B$, and $R^C$ are the same as or different from each other and each represent a hydrogen atom, a halogen atom, a cyano group, a nitro group, a protected amino group, a protected hydroxy group, a protected carboxy group, a $C_{1-6}$ alkyl group which may be substituted with one or more groups selected from the substituent group A, a $C_{2-6}$ alkenyl group which may be substituted with one or more groups selected from the substituent group A, an aryl group which may be substituted with one or more groups selected from the substituent group A, a $C_{1-6}$ alkoxy group which may be substituted with one or more groups selected from the substituent group A, an acyl group which may be substituted with one or more groups selected from the substituent group A, a $C_{1-6}$ alkylamino group which may be substituted with one or more groups selected from the substituent group A, a di($C_{1-6}$ alkyl)amino group which may be substituted with one or more groups selected from the substituent group A, a $C_{1-6}$ alkylthio group which may be substituted with one or more groups selected from the substituent group A, a $C_{1-6}$ alkylsulfonyl group which may be substituted with one or more groups selected from the substituent group A, an arylsulfonyl group which may be substituted with one or more groups selected from the substituent group A, or a heterocyclic group which may be substituted with one or more groups selected from the substituent group A; or $R^A$ and $R^B$ my be bonded to each other together with carbon atoms to which $R^A$ and $R^B$ are bonded and form a $C_{3-8}$ cycloalkyl ring which may be substituted with one or more groups selected from the substituent group A or a non-aromatic heterocyclic ring which may be substituted with one or more groups selected from the substituent group A.)

The compound represented by Formula (20) is preferably a compound in which $R^A$, $R^B$, and $R^C$ are the same as or different from each other and each represent a hydrogen atom, a halogen atom, a protected amino group, a protected hydroxy group, a protected carboxy group, a $C_{1-6}$ alkyl group which may be substituted with one or more groups selected from the substituent group A, an aryl group which may be substituted with one or more groups selected from the substituent group A, or a heterocyclic group which may be substituted with one or more groups selected from the substituent group A.

The compound represented by Formula (20) is preferably a compound in which $R^A$ and $R^B$ are bonded to each other together with carbon atoms to which $R^A$ and $R^B$ are bonded and each represent a $C_{5-8}$ cycloalkyl ring which may be substituted with one or more groups selected from the substituent group A or a non-aromatic heterocyclic ring which may be substituted with one or more groups selected from the substituent group A.

The compound represented by Formula (9) is preferably the following compound.

The compound represented by Formula (9) is preferably a compound in which $R^{1a}$ and $R^{1b}$ each represent a carboxy protective group.

The carboxy protective group represented by $R^{1a}$ and $R^{1b}$ is preferably a $C_{1-6}$ alkyl group which may be substituted with one or more groups selected from the substituent group A, a $C_{2-6}$ alkenyl group which may be substituted with one or more groups selected from the substituent group A, an aryl group which may be substituted with one or more groups selected from the substituent group A, an ar-$C_{1-6}$ alkyl group which may be substituted with one or more groups selected from the substituent group A, a $C_{1-6}$ alkoxy alkyl group which may be substituted with one or more groups selected from the substituent group A, or a silyl group which may be substituted with one or more groups selected from the substituent group A, more preferably a $C_{1-6}$ alkyl group which may be substituted with one or more groups selected from the substituent group A, even more preferably a $C_{1-6}$ alkyl group, and particularly preferably a $C_{1-3}$ alkyl group.

The $C_{1-6}$ alkyl group represented by $R^6$ may be substituted with one or more groups selected from the substituent group A.

The compound represented by Formula (9) is preferably a compound in which $R^6$ is a $C_{1-6}$ alkyl group which may be substituted with one or more groups selected from the substituent group B, more preferably a compound in which $R^6$ is a $C_{1-6}$ alkyl group, and even more preferably a compound in which $R^6$ is a $C_{1-3}$ alkyl group.

The amount of the compound represented by Formula (9) used is 1.0 time to 2.0 times as much as the amount of the compound represented by Formula (20) in terms of mole, preferably 1.0 time to 1.5 times as much as the amount of the compound in terms of mole, and more preferably 1.0 time to 1.2 times as much as the amount of the compound in terms of mole.

Examples of the base used in this reaction include inorganic bases. Among these, tert-butoxypotassium, sodium ethoxide, and sodium methoxide are preferable, and tert-butoxypotassium is more preferable.

The amount of the base used is 0.01 times to 5 times as much as the amount of the compound represented by Formula (20) in terms of mole, preferably 0.02 times to 2 times as much as the amount of the compound in terms of mole, and more preferably 0.03 times to 1 time as much as the amount of the compound in terms of mole.

The reaction temperature may be −20° C. to 100° C. preferably −10° C. to 80° C. and more preferably −5° C. to 60° C.

The reaction time may be 5 minutes to 50 hours, preferably 5 minutes to 24 hours, and more preferably 5 minutes to 6 hours.

Manufacturing Method 4
1,2-Diol group or 1,3-diol group protected with

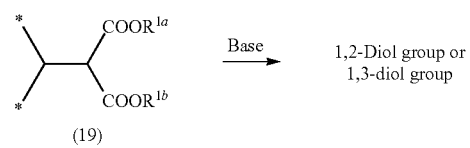

(In the formula, each of $R^{1a}$, $R^{1b}$, * has the same definition as described above.)

By reacting the 1,2-diol group or the 1,3-diol group, which is protected with the group represented by Formula (19), with a base, the protected diol group can be deprotected.

Specifically, by manufacturing the compound represented by Formula (20) by reacting the compound represented by Formula (21) with a base, the protected diol group can be deprotected.

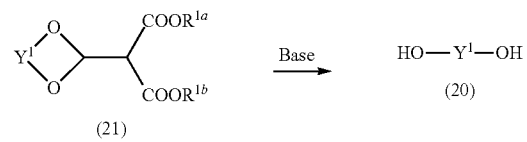

(In the formula, each of $R^{1a}$, $R^{1b}$, and $Y^1$ has the same definition as described above.)

The solvent used in this reaction is not particularly limited as long as the solvent does not affect the reaction. Examples of the solvent include aliphatic hydrocarbons, halogenated hydrocarbons, alcohols, ethers, esters, ketones, nitriles, amides, sulfoxides, aromatic hydrocarbons, ureas, and water. These solvents may be used by being mixed together.

Preferred examples of the solvent include alcohols, ethers, esters, ketones, nitriles, and water, and among these, alcohols, ethers, esters, and water are more preferable.

The amount of the solvent used is not particularly limited. The amount of the solvent used may be 1 time to 50 times (v/w) as much as the amount of the compound represented by Formula (21), and preferably 1 time to 15 times (v/w) as much as the amount of the compound.

Examples of the base used in this reaction include inorganic bases and organic bases. Among these, sodium hydrogen carbonate, sodium carbonate, potassium carbonate, sodium methoxide, propylamine, diethylamine, dibutylamine, triethylamine, diisopropylethylamine, pyridine, 2,6-lutidine, 4-dimethylaminopyridine, tetraethylammonium hydroxide, diazabicycloundecene, diazabicyclononene, guanidine, and morpholine are preferable, and sodium hydrogen carbonate, potassium carbonate, sodium methoxide, propylamine, diethylamine, dibutylamine, triethylamine, diisopropylethylamine, pyridine, and morpholine are more preferable.

The amount of the base used is 0.1 times to 5 times as much as the amount of the compound represented by Formula (21) in terms of mole, preferably 0.5 times to 2 times as much as the amount of the compound in terms of mole, and more preferably 0.8 times to 1.5 times as much as the amount of the compound in terms of mole.

The reaction temperature may be 0° C. to 150° C., preferably 10° C. to 100° C., and even more preferably 25° C. to 80° C.

The reaction time may be 5 minutes to 72 hours, preferably 30 minutes to 50 hours, and more preferably 1 hour to 24 hours.

The protective group for a diol group represented by Formula (19) is easily deprotected by a base. In contrast, the protective group for a diol group represented by Formula (19) is not deprotected in a step (for example, a hydrogenation reaction using a catalyst or a hydrolysis reaction performed in the presence of an acid) of deprotecting a benzylidene group widely used as a protective group for a diol group.

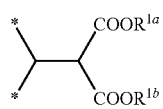

(19)

(In the formula, each, of $R^{1a}$, $R^{1b}$, and * has the same definition as described above.)

The use of the group represented by Formula (19) as a protective group for a diol group makes it possible to selectively protect and deprotect diol groups even in a case where two or more diol groups are present in a molecule.

The compounds obtained by the aforementioned manufacturing methods can be isolated and purified by a general method such as extraction, crystallization, distillation, or column chromatography. Furthermore, the compounds obtained by the aforementioned manufacturing methods may be used as they are in the next reaction without being isolated.

In a case where crystalline polymorphs, hydrates, or solvates are present in the compounds obtained by the aforementioned manufacturing methods, all of the crystal forms, hydrates, and solvates can be used in the present invention.

Next, the present invention will be described based on reference examples and examples, but the present invention is not limited thereto.

EXAMPLES

Unless otherwise specified, as a carrier for silica gel column chromatography, an FR-260 HI-FLAS™ COLUMN manufactured by YAMAZEN CORPORATION and WAKOGEL C-200 manufactured by Wako Pure Chemical Industries, Ltd. was used.

A mixing ratio in an eluant is volume ratio. For example, "hexane/ethyl acetate=90/10 to 50/50" means an eluant of 90% hexane/10% ethyl acetate is finally changed to an eluant of 50% hexane/50% ethyl acetate.

An NMR spectrum was measured using tetramethylsilane as an internal standard and using BRUKER AV300 (Bruker Corporation) or JNM-AL400 model (JEOL Ltd.), and all of the δ values were expressed using ppm.

Each abbreviation in each example means the following.
Ac: acetyl
Bn: benzyl
Et: ethyl
Me: methyl
Ph: phenyl
PMB: 4-methoxybenzyl
Tol: p-toluoyl
Ts: 4-methylbenzenesulfonyl
DMSO-$D_6$: deuterated dimethyl sulfoxide
pyridine-$D_5$: deuterated pyridine
HPLC: high performance liquid chromatography Reference Example 1

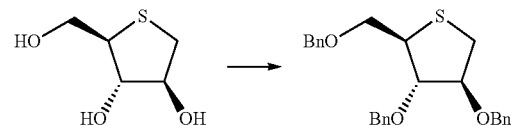 [SMILES: OC[C@H]1SC[C@@H](O)[C@@H]1O ; c1ccc(COC[C@H]2SC[C@@H](OCc3ccccc3)[C@@H]2OCc2ccccc2)cc1]

2.00 g of 60% sodium hydride was added to 15 mL of a N,N-dimethylformamide solution containing 1.50 g of (2R,3S,4S)-2-(hydroxymethyl)tetrahydrothiophene-3,4-diol at 0° C., and the resulting mixture was stirred for 1 hour at a temperature of equal to or lower than 5° C. Then, 4.50 mL of benzyl bromide was added thereto at 0° C., followed by stirring for 3 hours at 25° C. Ethyl acetate and water were added to the reaction mixture. An organic layer was collected by separation, washed with a saturated aqueous sodium chloride solution, and dried over anhydrous magnesium sulfate, and the solvent was distilled away under reduced pressure. The obtained residue was purified by column chromatography (hexane/ethyl acetate=95/5 to 86/14), thereby obtaining 2.31 g of (2R,3S,4S)-3,4-bis(benzyloxy)-2-((benzyloxy)methyl)tetrahydrothiophene as a colorless oily substance.

$^1$H-NMR (CDCl$_3$) δ values: 2.90 (1H, dd, J=4.8, 11.4 Hz), 3.04 (1H, M, J=5.0, 11.4 Hz), 3.47-3.59 (2H, m), 3.69 (1H, t, J=7.8 Hz), 4.10-4.21 (2H, m), 4.45-4.61 (6H; m), 7.25-7.35 (15H, m).

Reference Example 2

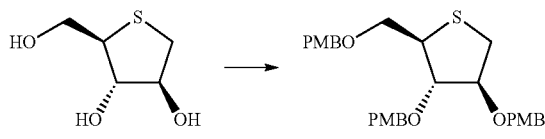

1.49 g of 60% sodium hydride was added to 10 mL of a N,N-dimethylformamide solution containing 1.12 g of (2R, 3S,4S)-2-(hydroxymethyl)tetrahydrothiophene-3,4-diol at 0° C., and the resulting mixture was stirred for 30 minutes at a temperature of equal to or lower than 5° C. then, 3.86 mL of 4-methoxybenzyl chloride was added thereto at 0° C., followed by stirring for 6 hours at 25° C. Ethyl acetate and water were added to the reaction mixture. An organic layer was collected by separation, washed with a saturated aqueous sodium chloride solution, and dried over anhydrous magnesium sulfate, and the solvent was distilled away under reduced pressure. The obtained residue was purified by column chromatography (hexane/ethyl acetate=95/5 to 86/14), thereby obtaining 1.93 g of (2R,3S,4S)-3,4-bis((4-methoxybenzyl)oxy)-2-(((4-methoxybenzyl)oxy)methyl) tetrahydrothiophene as a colorless oily substance.

$^1$H-NMR (CDCl$_3$) δ values: 2.86 (1H, dd, J=4.8, 11.4 Hz), 3.03 (1H, dd, J=5.2, 11.4 Hz), 3.42-3.52 (2H, m), 3.64 (1H, dd, J=7.2, 8.1 Hz), 3.79-3.81 (9H, m), 4.03-4.16 (2H, m), 4.39-4.52 (6H, m), 6.84-6.87 (6H, m), 7.18-7.25 (6H, m).

Example 1

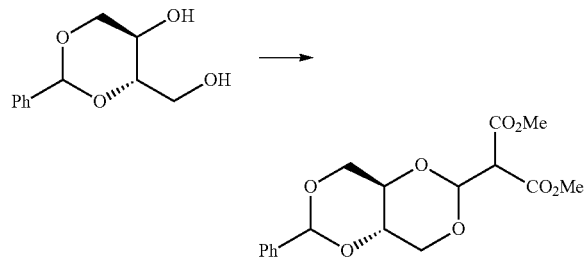

1.1 g of tert-butoxypotassium was added to 200 mL of a tetrahydrofuran solution containing 20.0 g of (4S,5R)-4-(hydroxymethyl)-2-phenyl-1,3-dioxan-5-ol and 18.2 g of dimethyl methoxymethylene malonate at 25° C., and the resulting mixture was stirred for 1 hour at 25° C. Toluene was added to the reaction mixture, tetrahydrofuran was distilled away under reduced pressure, and then ethyl acetate and water were added thereto. An organic layer was collected by separation, washed sequentially with water and then with a saturated aqueous sodium chloride solution, and dried over anhydrous magnesium sulfate, and the solvent was distilled away under reduced pressure. The obtained residue was recrystallized from methanol, thereby obtaining 21.3 g of dimethyl 2-((4aS,8aR)-6-phenyltetrahydro[1,3]dioxino[5,4-d][1,3]dioxin-2-yl)malonate as a white solid.

$^1$H-NMR (CDCl$_3$) δ values: 3.73-3.81 (11H, m), 4.23-4.31 (2H, m), 5.30 (1H, d, J=7.8 Hz), 5.60 (1H, s), 7.35-7.39 (3H, m), 7.44-7.50 (2H, m).

Example 2

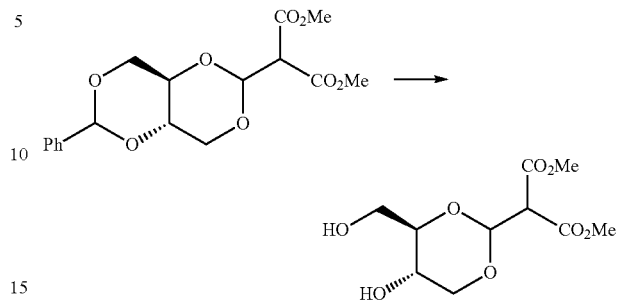

1.24 g of 20% palladium hydroxide/carbon was added to 70 mL of an ethyl acetate solution containing 20.4 g of dimethyl 2-((4aS,8aR)-6-phenyltetrahydro[1,3]dioxino[5,4-d][1,3]dioxin-2-yl)malonate at 25° C., and the resulting mixture was stirred for 4 hours in a hydrogen atmosphere (5 MPa). After insoluble matters were removed by filtration, the solvent was distilled away under reduced pressure, thereby obtaining 15.7 g of dimethyl 2-((4R,5S)-5-hydroxy-4-(hydroxymethyl)-1,3-dioxan-2-yl)malonate as a colorless oily substance.

$^1$H-NMR (CDCl$_3$) δ values: 2.40 (1H, s), 2.70 (1H, s), 3.44-3.56 (2H, m), 3.68 (1H, d, J=7.2 Hz), 3.76-3.85 (9H, m), 4.11-4.21 (1H, m), 5.15 (1H, d, J=7.2 Hz).

Example 3

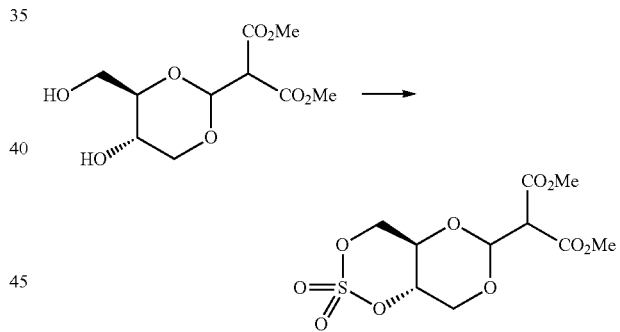

112 mL of triethylamine was added to 800 mL of a methylene chloride solution containing 53.0 g of dimethyl 2-((4R,5S)-5-hydroxy-4-(hydroxymethyl)-1,3-dioxan-2-yl) malonate of a temperature of equal to or lower than −5° C., and than 500 mL of a methylene chloride solution containing 21.8 mL of thionyl chloride was added dropwise thereto at a temperature of equal to or lower than −5° C. The reaction mixture was stirred for 20 minutes at a temperature of equal to or lower than 5° C., and then water was added thereto. An organic layer was collected by separation and washed sequentially with 1 mol/L hydrochloric acid, water, and then a saturated aqueous sodium hydrogen carbonate solution, and the solvent vas distilled away under reduced pressure.

A mixed solution of 265 mL of methylene chloride containing the obtained residue and 265 mL of acetonitrile was added dropwise to 530 mL of water containing 159 g of sodium periodate and 1.25 g of a ruthenium (III) chloride n-hydrate at 0° C., followed by stirring for 20 minutes. Ethyl acetate was added to the reaction mixture. An organic layer was collected by separation, washed sequentially with water, a 10% aqueous sodium thiosulfate solution, and then a saturated aqueous sodium chloride solution, and anhydrous magnesium sulfate and silica gel were added thereto, followed by stirring for 5 minutes. After insoluble matters were removed by filtration, the solvent was distilled away under reduced pressure, and the obtained residue was recrystallized from methanol and a water, thereby obtaining 42.3 g of dimethyl 2-((4aR,8aS)-2,2-dioxidotetrahydro[1,3]dioxino[5,4-d][1,3,2]dioxathiin-6-yl)malonate as a white solid.

$^1$H-NMR (CDCl$_3$) δ values: 3.70 (1H, d, J=7.8 Hz), 3.77 (3H, s), 3.78 (3H, s), 3.82 (1H, d, J=10.5 Hz), 4.01-4.11 (1H, m), 4.31 (1H, dd, J=5.0, 10.5 Hz), 4.56 (1H, dd, J=5.0, 10.5 Hz), 4.54-4.75 (2H, m), 5.27 (1H, d, J=7.8 Hz).

Example 4

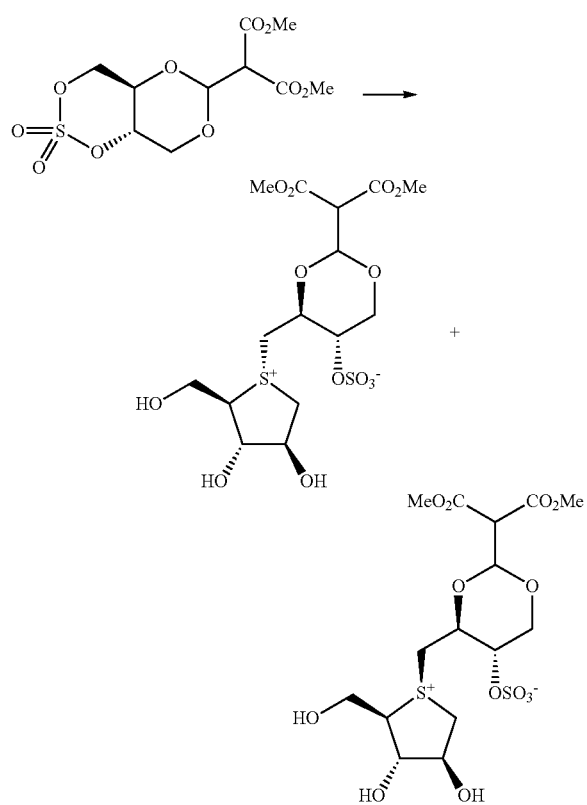

31 μL, of 2,6-lutidine was added to 1.5 mL of an acetone solution containing 500 mg of (2R,3S,4S)-2-(hydroxymethyl)tetrahydrothiophene-3,4-diol and 1.14 g of dimethyl 2-((4aR,8aS)-2,2-dioxidotetrahydro[1,3]dioxino[5,4-d][1,3,2]dioxathiin-6-yl)malonate at 25° C., followed by stirring for 13 hours at 70° C. The reaction mixture was cooled to room temperature, acetone was added thereto, and solids were collected by filtration, thereby obtaining 1.20 g of (4S,5S)-4-(((2R,3S,4S)-3,4-dihydroxy-2-(hydroxymethyl) tetrahydro-1H-thiophen-1-ium-1-yl) methyl-2-(1,3-dimethoxy-1,3-dioxopropan-2-yl)-1,3-dioxan-5-yl sulfate as a white solid.

As a result of measuring $^1$H-NMR and HPLC, it was confirmed that a ratio of trans/cis was 78/22.

$^1$H-NMR (DMSO-D$_6$) δ values: 3.56-3.63 (2H, m), 3.62-3.73 (8H, m) 3.42-4.08 (6H, m), 4.14 (1H, dd, J=5.3, 10.2 Hz), 4.22-4.29 (2H, m), 4.47-4.53 (1H, m), 5.21 (1H, d, J=7.5 Hz), 5.57 2H, m), 6.13 (2H, m).

Example 5

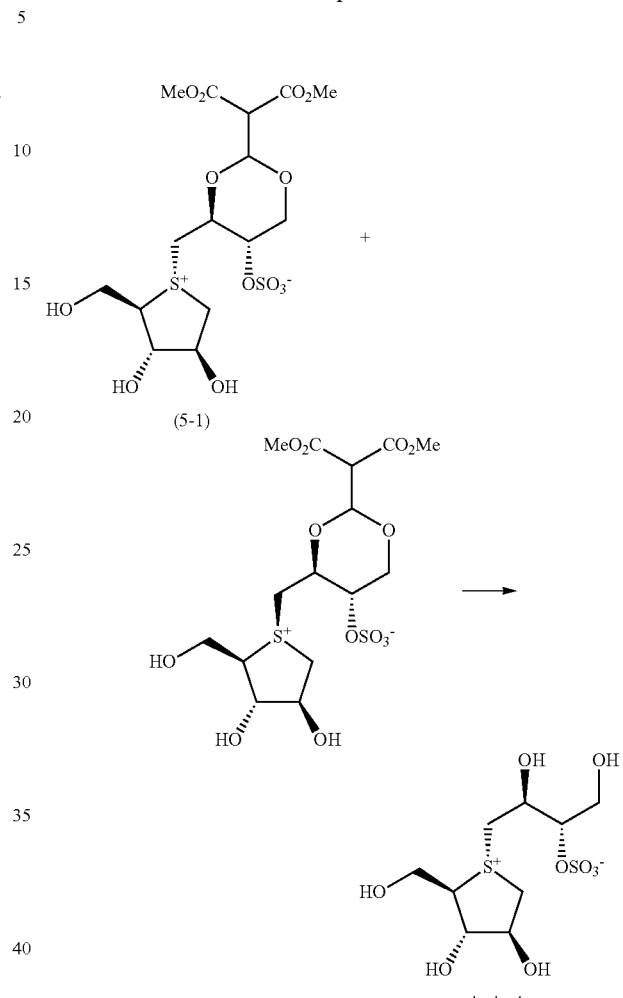

756 μL of diethylamine was added to a mixed solution of 14.5 mL of water and 14.5 mL of ethyl acetate containing 2.90 g of (4S,5S)-4-(((2R,3S,4S)-3,4-dihydroxy-2-(hydroxymethyl)tetrahydro-1H-thiophen-1-ium-1-yl) methyl-2-(1,3-dimethoxy-1,3-dioxopropan-2-yl)-1,3-dioxan-5-yl sulfate (trans/cis=78/22) at 25° C., followed by stirring for 50 minutes at 25° C. An aqueous layer was collected by separation and washed with ethyl acetate, and the solvent was distilled away under reduced pressure. The obtained residue was recrystallized from methanol, thereby obtaining 1.05 g of (2S,3S)-4-((1S,2R,3S,4S)-3,4-dihydroxy-2-(hydroxymethyl)tetrahydro-1H-thiophen-1-ium-1-yl)-1,3-dihydroxybutan-2-yl sulfate (salacinol) as a white solid.

$^1$H-NMR (pyridine-D$_5$) δ values: 4.32-4.39 (3H, m), 4.51-4.66 (5H, m), 4.75-4.82 (1H, m), 4.91-5.05 (1H, m), 5.09-5.14 (2H, m), 5.23-5.27 (1H, m).

220 μL of triethylamine was added to a mixed solution of 2.5 mL of water and 2.5 mL of methanol containing 500 mg of (4S,5S)-4-(((2R,3S,4S)-3,4-dihydroxymethyl)tetrahydro-1H-thiophen-1-ium-1-yl) methyl-2-(1,3-dimethoxy-1,3-dioxopropan-2-yl)-1,3-dioxan-5-yl sulfate (trans/cis=78/22) at 25° C. followed by stirring for 5 hours at 25° C. Ethyl acetate was added to the reaction mixture. An aqueous layer was collected by separation and washed with ethyl acetate, and the solvent was distilled away under reduced pressure.

As a result of measuring the obtained residue by HPLC, it was confirmed that salacinol was generated, and the reaction rate was 97%.

(5-3)

220 μL of propyl amine was added to a mixed solution of 2.5 mL of water and 2.5 mL of toluene containing 500 mg of (4S,5S)-4-(((2R,3S,4S)-3,4-dihydroxy-2-yl)-1,3-dioxan-5-yl sulfate (trans/cis=78/22) at 25° C., followed by stirring for 1 hour at 25° C. Toluene was added to the reaction mixture. An aqueous layer was collected by separation, and the solvent was distilled away under reduced pressure.

As a result of measuring the obtained residue by HPLC, it was confirmed that salacinol was generated, and the reaction rate was 96%.

(5-4)

212 μL of dibutylamine was added to a mixed solution of 2.5 mL of water and 2.5 mL of toluene containing 300 mg of (4S,5S)-4-(((2R,3S,4S)-3,4-dihydroxy-2-(hydroxyethyl)tetrahydro-1H-thiophen-1-ium-1-yl) methyl-2-(1,3-dimethoxy-1,3-dioxopropan-2-yl)-1,3-dioxan-5-yl) sulfate (trans/cis=78/22) at 25° C., followed by stirring for 4 hours at 25° C. Toluene was added to the reaction mixture. An aqueous layer was collected by separation, and the solvent was distilled away under reduced pressure.

As a result of measuring the obtained residue by HPLC, it was confirmed that salacinol was generated, and the reaction rate was 85%.

(5-5)

10 mL of an aqueous solution containing 1 g of (4S,5S)-4-(((2R,3S,4S)-3,4-dihydroxy-2-(hydroxymethyl)tetrahydro-1H-thiophen-1-ium-1-yl) methyl-2-(1,3-dimethoxy-1,3-dioxopropan-2-yl)-1,3-dioxan-5-yl sulfate (trans/cis=78/22) was stirred for 8 hours at 70° C., and then the solvent was distilled away under reduced pressure. 203 μL of pyridine and 287 μL of aniline were added to a mixed solution of 5 mL of water and 5 mL of methanol containing the obtained oily substance at 25° C., followed by stirring for 13 hours at 50° C. Toluene was added to the reaction mixture. An aqueous layer was collected by separation and washed with ethyl acetate, and the solvent was distilled away under reduced pressure.

The obtained residue was recrystallized from methanol, thereby obtaining 485 mg of salacinol as a white solid.

Example 6

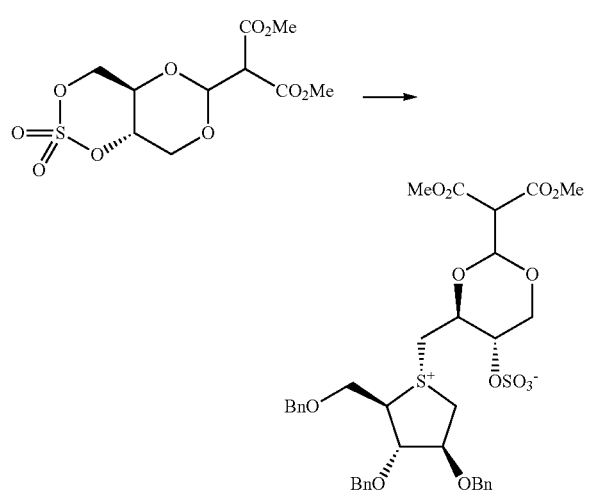

31 μL of 2,6-lutidine was added to 1.5 mL of acetone solution containing 1.24 g of (2R,3S,4S)-3,4-bis(benzyloxy)-2-((benzyloxy)methyl)tetrahydrothiophene and 1.01 g of dimethyl 2-(4aR,8aS)-2,2-dioxidotetrahydro[1,3]dioxino[5,4-d][1,3,2]dioxathiin-6-yl)malonate at 25° C., followed by stirring for 24 hours at 70° C. The reaction mixture was cooled to room temperature, and the solvent was distilled away under reduced pressure. The obtained residue was purified by column chromatography (chloroform/methanol=99/1 to 95/5), thereby obtaining 1.32 g of (4S,5S)-4-(((1S,2R,3S,4S)-3,4-bis(benzyloxy)-2-((benzyloxy)methyl)tetrahydro-1H-thiophen-1-ium-1-yl)methyl)-2-(1,3-dimethoxy-1,3-dioxopropan-2-yl)-1,3-dioxan-5-yl sulfate as a colorless oily substance.

$^1$H-NMR (DMSO-$D_6$) δ values: 3.56-3.66 (7H, m), 3.72-376 (2H, m), 3.88-4.16 (7H, m), 4.24-4.38 (2H, m), 4.51-4.64 (7H, m), 4.76-4.79 (1H, m), 5.17 (1H, d, J=7.2 Hz), 7.33-7.37 (15H, m).

Example 7

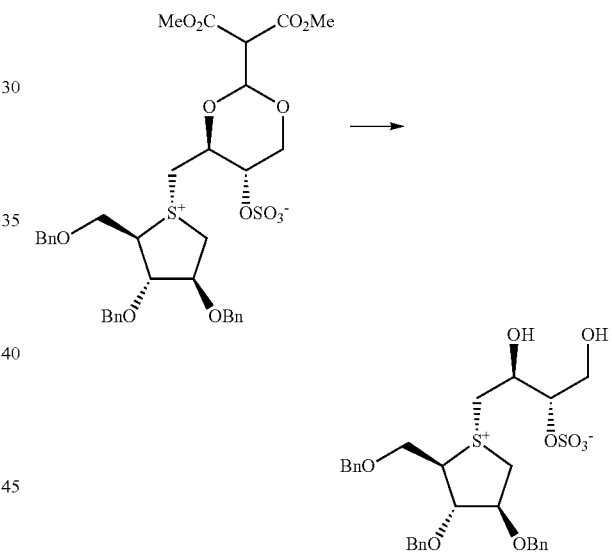

73 μL of diethylamide was added to 4.4 mL of a methanol solution containing 440 mg of (4S,5S)-4-(((1S,2R,3S,4S)-3,4-bis(benzyloxy)-2-((benzyloxy)methyl)tetrahydro-1H-thiophen-1-ium-1-yl)methyl)-2-(1,3-dimethoxy-1,3-dioxopropan-2-yl)-1,3-dioxan-5-yl sulfate at 25° C., followed by stirring for 1 hour at 25° C. The solvent of the reaction mixture was distilled away under reduced pressure, and the obtained residue was purified by column chromatography (chloroform/methanol=100/0 to 92/8), thereby obtaining 240 mg of (2S,3S)-4-((1R,2R,3S,4S)-3,4-bis(benzyloxy)-2-((benzyloxy)methyl)tetrahydro-1H-thiophen-1-ium-1-yl)-1,3-dihydroxybutan-2-yl sulfate as a white solid.

$^1$H-NMR (DMSO-$D_6$) δ values: 3.61-3.65 (2H, m), 3.74-4.05 (6H, m) 4.09-4.14 (1H, m), 4.17-4.23 (1H, m), 4.36-4.41 (1H, m), 4.50-4.80 (9H, m), 6.01 (1H, d, J=6.0 Hz), 7.23-7.39 (15H, m).

Example 8

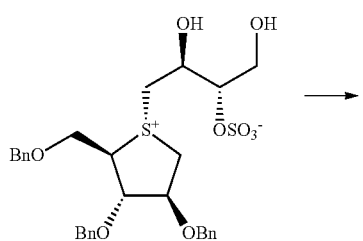

salacinol 24 mg of 20% palladium hydroxide/carbon was added to 1 mL of acetic acid solution containing 240 mg of (2S,3S)-4-((1R,2R,3S,4)-3-bis(benzyloxy)-2-((benzyloxy)methyl)tetrahydro-1H-thiophen-1-ium-1-yl)-1,3-dihydroxybutan-2-yl sulfate at 25° C., followed by stirring for 2 hours at 50° C. in a hydrogen atmosphere. The reaction mixture was cooled to room temperature, and insoluble matters were removed by filtration.

As a result of measuring $^1$H-NMR and HPLC, it was confirmed that the raw material disappeared, and salacinol was generated.

Example 9

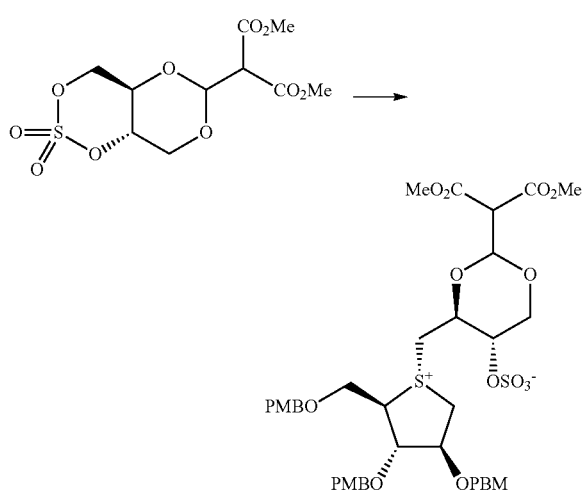

18 μL of 2,6-lutidine was added to 1 mL of an acetone solution containing 1.00 g of (2R,3S,4S)-3,4-bis((4-methoxybenzyl)oxy)-2-(((4-methoxybenzyl)oxy)methyl)tetrahydrothiophene and 671 mg of dimethyl 2-((4aR,8aS)-2,2-dioxidotetrahydro[1,3]dioxino[5,4-d][1,3,2]dioxathiin-6-yl)malonate at 25° C., followed by stirring for 13 hours at 70° C. The reaction mixture was cooled to room temperature, and the solvent was distilled away under reduced pressure. The obtained residue was purified by column chromatography (chloroform/methanol=90/10), thereby obtaining 1.10 g of (4S,5S)-4-(((1S,2R,3S,4S)-3,4-bis((4-methoxybenzyl)oxy)-2-(((4-methoxybenzyl)oxy)methyl)tetrahydro-1H-thiophen-1-ium-1-yl)methyl)-2-(1,3-dimethoxy-1,3-dioxopropan-2-yl)-1,3-dioxan-5-yl sulfate as a white solid.

$^1$H-NMR (DMSO-D$_6$) δ values: 3.52-4.17 (25H, m), 4.21-4.28 (2H, m), 4.41-4.58 (7H, m), 4.64-4.69 (1H, m), 5.16 (1H, d, J=7.5 Hz), 6.88-6.93 (6H, m), 7.16-7.28 (6H, m).

Example 10

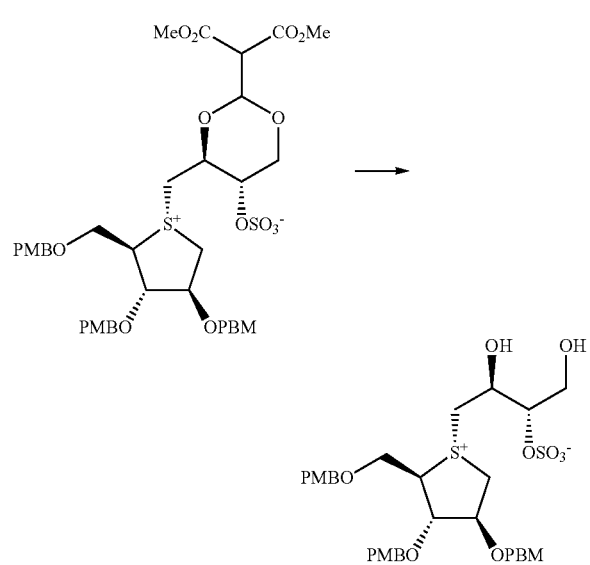

74 μL of diethylamine was added to 5.0 mL of a methanol solution containing 500 mg of (4S,5S)-4-(((1S,2R,3S,4S)-3,4-bis((4-methoxybenzyl)oxy-2-(((4-methoxybenzyl)oxy)methyl) tetrahydro-1H-thiophen-1-ium-1-yl)methyl)-2-(1,3-dimethoxy-1,3-dioxopropan-2-yl)-1,3-dioxan-5-yl sulfate at 25° C., followed by stirring for 3 hours at 25° C. The solvent of the reaction mixture was distilled away under reduced pressure, and the obtained residue was purified by column chromatography (chloroform/methanol=100/0 to 94/6), thereby obtaining 300 mg of (2S,3S)-4-((1R,2R,3S,4S)-3,4-bis((4-methoxybenzyl)oxy)-2-(((4-methoxybenzyl)oxy)methyl)tetrahydro-1H-thiophen-1-ium-1-yl)-1,3-dihydroxybutan-2-yl sulfate as a white solid.

$^1$H-NMR (DMSO-D$_6$) δ values: 3.49-3.99 (17H, m) 4.06-4.21 (2H, m) 4.28-4.31 (1H, m), 4.38-4.66 (8H, m), 4.76-4.79 (1H, m), 6.00 (1H, d, J=6.0 Hz), 6.30-6.93 (6H, m), 7.16-7.28 (6H, m).

Example 11

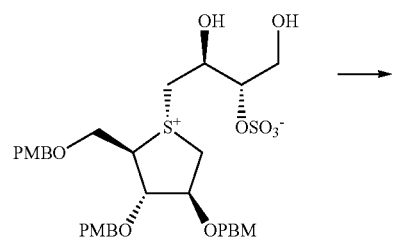

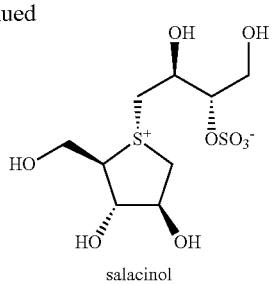

salacinol

A mixed solution of 1.2 mL of trifluoroacetic acid and 0.2 L of water containing 300 mg of (2S,3S)-4-((1R,2R,3S,4S)-3,4-bis((4-methoxybenzyl)oxy)-2-(((4-methoxybenzyl)oxy)methyl)tetrahydro-1H-thiophen-1-ium-1-yl)-1,3-dihydroxybutan-2-yl sulfate was stirred for 2 hours at 25° C.

As a result of measuring $^1$H-NMR and HPLC, it was confirmed that the raw material disappeared, and salacinol was generated.

Example 12

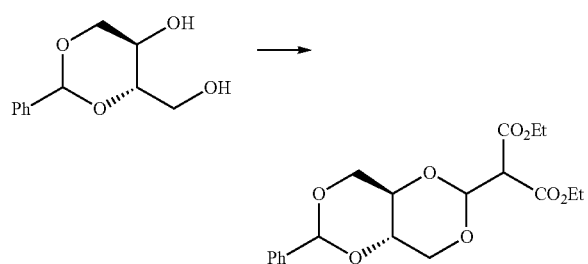

267 mg of tert-butoxypotassium was added to 50 mL of a tetrahydrofuran solution containing 5.00 g of (4S,5R)-4-(hydroxymethyl)-2-phenyl-1,3-dioxan-5-ol and 5.7 g diethyl ethoxymethylene malonate at 25° C., followed by stirring for 1 hour at 25° C. Toluene was added to the reaction mixture, tetrahydrofuran was distilled away under reduced pressure, and then ethyl acetate and water were added thereto. An organic layer was collected by separation, washed sequentially with water and a saturated aqueous sodium chloride solution, and dried over anhydrous magnesium sulfate, and the solvent was distilled away under reduced pressure. The obtained residue was purified by column chromatography (hexane/ethyl acetate=16/84 to 33/67), thereby obtaining 3.54 g of diethyl 2-((4aS,8aR)-6-phenyltetrahydro[1,3]dioxino[5,4-d][1,3]dioxin-2-yl)malonate as a white solid.

$^1$H-NMR (CDCl$_3$) δ values: 1.24-1.31 (6H, m) 3.65 (1H, d, J=7.8 Hz), 3.65-3.82 (4H, m), 4.19-4.27 (6H, m), 5.30 (1H, d, J=7.8 Hz), 5.61 (1H, s), 7.35-7.39 (3H, m), 7.45-7.49 (2H, m).

Example 13

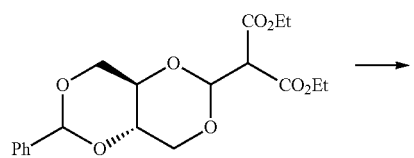

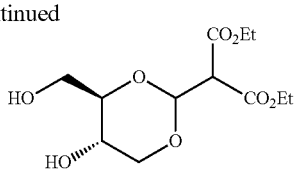

800 μL of a 0.5 mol/L hydrochloric acid/methanol solution to 18 mL of a methanol solution containing 3.54 g of diethyl 2-((4aS,8aR)-6-phenyltetrahydro[1,3]dioxino[5,4][1,3]dioxin-2-yl)malonate at 25° C., followed by stirring for 3 hours at 25° C. 50 μL of triethylamine was added to the reaction mixture, and the solvent was distilled away under reduced pressure. The obtained residue was purified by column chromatography (hexane/ethyl acetate=33/67 to 0/100), thereby obtaining 2.45 g of diethyl 2-((4R,5S)-5-hydroxy-4-(hydroxymethyl)-1,3-dioxan-2-yl)malonate as a colorless oily substance.

$^1$H-NMR (CDCl$_3$) δ values: 1.24-1.30 (6H, m) 2.37 (1H, s), 2.75 (1H, s), 3.44-3.56 (2H, m), 3.63 (1H, d, J=7.5 Hz), 3.78-3.86 (3H, m) 4.16-4.26 (5H, m), 5.15 (1H, d, J=7.5 Hz).

Example 14

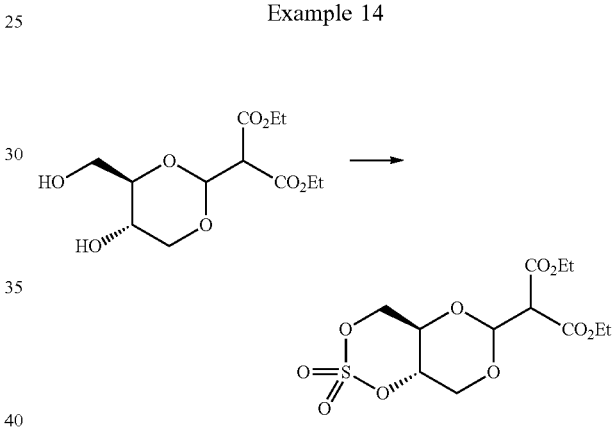

4.44 mL of triethylamine was added to 40 mL of a methylene chloride solution containing 2.45 g of diethyl 2-((4R,5S)-5-hydroxy-4-(hydroxymethyl)-1,3-dioxan-2-yl) malonate at a temperature of equal to or lower than −5° C. and then 21 mL of a methylene chloride dilution containing 913 μL of thionyl chloride was added dropwise thereto at a temperature of equal to or lower than −5° C. The reaction mixture was stirred for 20 minutes at a temperature of equal to or lower than 5° C., water was added thereto. An organic layer was collected by separation and then washed sequentially with 1 mol/L hydrochloric acid, a saturated aqueous sodium hydrogen carbonate solution, and a saturated aqueous sodium chloride solution, and the solvent was distilled away under reduced pressure.

A mixed solution of 10 mL of methylene chloride and 10 mL of acetonitrile containing the obtained residue was added dropwise to 25 mL of an aqueous solution containing 6.64 g of sodium periodate and 52.2 mg of ruthenium (III) chloride n-hydrate at 0° C., followed by stirring for 20 minutes. Ethyl acetate was added to the reaction mixture. An organic layer was collected by separation and washed sequentially with water, a 10% aqueous sodium thiosulfate solution, and a saturated aqueous sodium chloride solution, and anhydrous magnesium sulfate and silica gel were added thereto, followed by stirring for 5 minutes. After insoluble matters were removed by filtration, the solvent was distilled away under reduced pressure. The obtained residue was purified by column chromatography (hexane/ethyl acetate=84/16 to 60/40), thereby obtaining 2.10 g of diethyl 2-((4aR,8aS)-2,2-dioxidotetrahydro[1,3]dioxino[5,4-d][1,3,2]dioxathiin-6-yl)malonate as a white solid.

¹H-NMR (CDCl₃) δ values: (1.25-1.30 (6H, m), 3.65 (1H, d, J=7.8 Hz), 3.80 (1H, dd, J=10.5, 10.5 Hz), 4.02-4.11 (1H, m), 4.18-4.35 (5H, m), 4.52-4.57 (1H, m), 4.63-4.72 (2H, m), 5.26 (1H, d, J=7.8 Hz).

Example 15

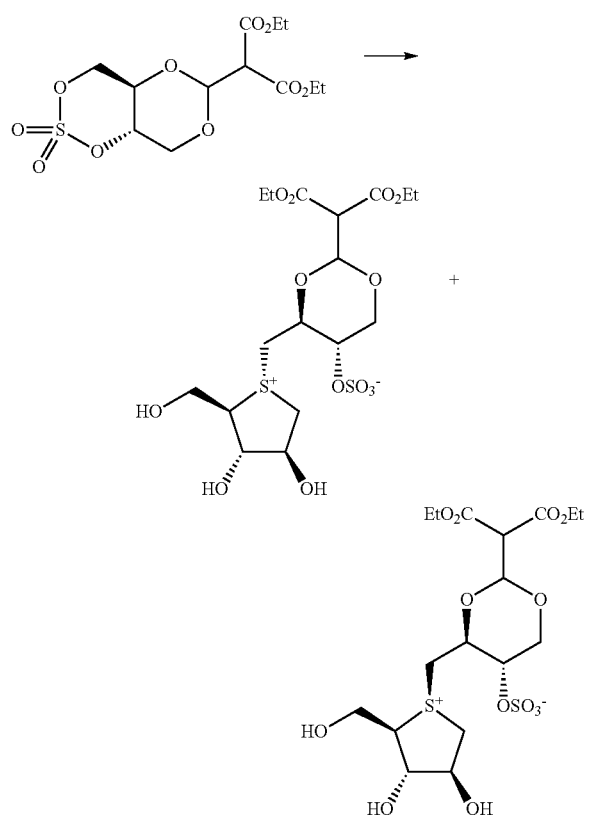

31 μL of 2,6-lutidine was added to 1.5 mL of an acetone solution containing 500 mg of (2R,3S,4S)-2-(hydroxymethyl)tetrahydrothiophene-3,4-diol and 1.24 g of diethyl 2-((4aR,8aS)-2,2-dioxidotetrahydro[1,3]dioxino[5,4-d][1,3,2]dioxathiin-6-yl)malonate at 25° C., followed by stirring for 13 hours at 70° C. The reaction mixture was cooled to room temperature, acetone was added thereto, and solids were collected by filtration, thereby obtaining 1.01 g of (4S,5S)-2-(1,3-diethoxy-1,3-dioxopropan-2-yl)-4-(((2R,3S,4S)-3,4-dihydroxy-2-(hydroxymethyl)tetrahydro-1H-thiophen-1-ium-1-yl)methyl)-1,3-dioxan-5-yl sulfate as a white solid. As a result of measuring ¹H-NMR, it was confirmed that a ratio of trans/cis in this compound was 81/19.

¹H-NMR (DMSO-D₆) δ values: 1.19 (6H, dd, J=7.0, 13.6 Hz), 3.54-4.21 (17H, m), 4.45-4.51 (1H, m), 5.20 (1H, m), 5.68-5.71 (1H, m), 6.12-6.14 (2H, m).

Example 16

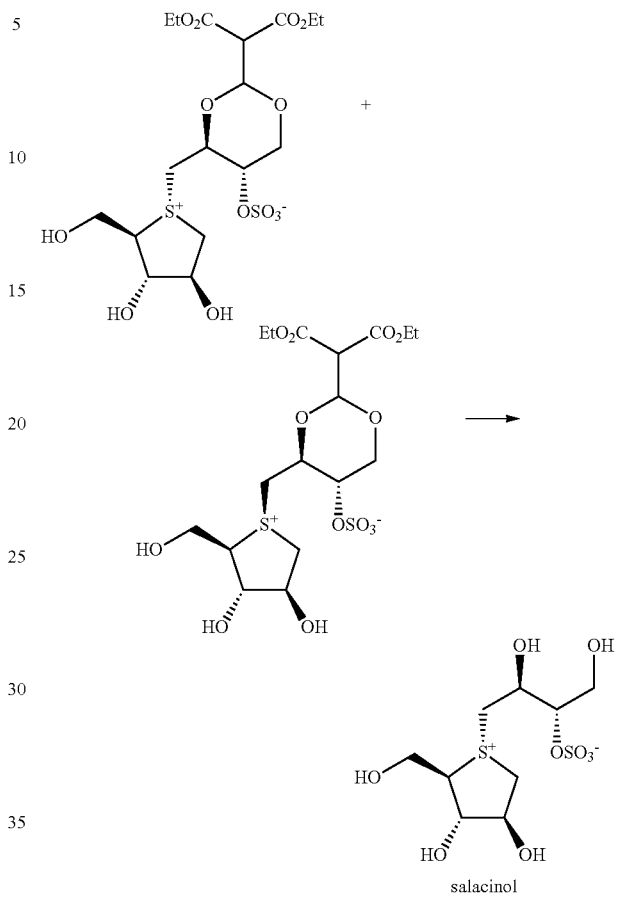

123 μL of diethylamine was added to a mixed solution of 2.5 mL of water and 2.5 mL of ethyl acetate containing 500 mg of (4S,5S)-2-(1,3-diethoxy-1,3-dioxopropan-2-yl)-4-(((2R,3S,4S)-3,4-dihydroxy-2-(hydroxymethyl)tetrahydro-1H-thiophen-1-ium-1-yl)methyl)-1,3-dioxan-5-yl sulfate (trans/cis=81/19) at 25° C., followed by stirring for 9 hours at 25° C. An aqueous layer was collected by separation and washed with ethyl acetate, and the solvent was distilled away under reduced pressure.

As a result of measuring ¹H-NMR and HPLC of the obtained residue, it was confirmed that salacinol was generated, and the reaction rate was 97%.

Example 17

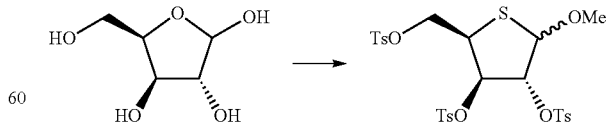

22.0 mL of acetyl chloride was added dropwise to 840 mL of a methanol solution containing 120 g of (3R,4R,5R)-5-(hydroxymethyl)tetrahydrofuran-2,3,4-triol at a temperature of equal to or lower than 10° C., followed by stirring for 2 hours at a temperature of 20° C. to 30° C. 63 mL of a 28% sodium methoxide methanol solution was added to the reaction mixture, methanol was distilled away under reduced pressure, and 800 mL of acetonitrile and 480 g of p-toluenesulfonyl chloride were added thereto. In a state where the internal temperature was kept at a temperature of equal to or lower than 25° C., a mixture of 323 mL of triethylamine and 25.2 mL of N-methylimidazole was added dropwise thereto, followed by stirring for 2.5 hours at 30° C. 900 mL of water was added to the reaction mixture, followed by stirring for 2 hours at 30° C., and ethyl acetate was added thereto. An organic layer was collected by separation, washed with a 25% aqueous sodium chloride solution, and dried over anhydrous magnesium sulfate, and the solvent was removed under reduced pressure. 1.9 L of ethanol was added to the obtained residue and dissolved by heating, and the resulting mixture was crystallized while being cooled. 800 mL of methanol was added thereto at an internal temperature of 35° C., followed by stirring for 2 hours at 25° C. Solids were collected by filtration, thereby obtaining 47 g of (3R,4S,5R)-2-methoxy-5-(((4-methylphenyl)sulfonyloxy)methyl)tetrahydrofuran-3,4-diyl bis(4-methylbenzenesulfonate) as a white solid.

$^1$H-NMR (CDCl$_3$) δ values: 7.77-7.64 (6H, m), 7.41-7.32 (6H, m), 5.04 (0.26H, t, J=6.9 Hz), 4.79 (0.74H, dd, J=1.2, 6.0 Hz), 4.80-4.65 (2H, m), 4.43 (0.74H, m), 4.34 (0.26H, m), 4.25-4.14 (0.26H, m), 4.12-4.04 (1.74H, m), 3.21 (0.78H, s), 3.16 (2.22H, s), 2.48-2.45 (3H, m).

Example 18

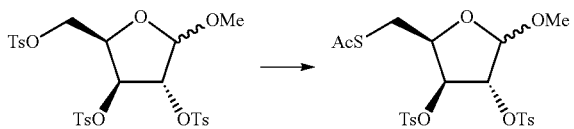

65.6 g of S-potassium thioacetate was added to 585 mL of a N,N-dimethylformamide solution containing 200 g of (3R,4S,5R)-2-methoxy-5-(((4-methylphenyl)sulfonyloxy)methyl)tetrahydrofuran-3,4-diyl bis(4-methylbenzenesulfonate) in a nitrogen atmosphere, followed by stirring for 2 hours at 70° C. the reaction mixture was cooled to room temperature, and water, a 25% aqueous sodium chloride solution, and ethyl acetate were added thereto. An organic layer was collected by separation, washed sequentially with a 7.5% aqueous sodium hydrogen carbonate solution, 1 mol/L hydrochloric acid, and a 25% aqueous sodium chloride solution, treated with 3 g of activated carbon, and then dried over anhydrous magnesium sulfate, and the solvent was distilled away under reduced pressure. As a result, 161.5 g of S-(((2S,3S,4R)-5-methoxy-3,4-bis((4-methylphenyl)sulfonyloxy)tetrahydrofuran-2-yl)methyl) ethanethioate as a reddish brown oily substance was obtained.

$^1$H-NMR (CDCl$_3$) δ values: 7.79-7.69 (4H, m), 7.40-7.32 (4H, m), 5.04-4.75 (3H, m), 4.33-4.26 (1H, m), 3.24 (2.13H, s), 3.22 (0.87H, s), 3.19-2.98 (2H, m), 2.75-2.45 (6H, m), 2.31 (0.87H, s), 2.29 (2.13H, s).

Example 19

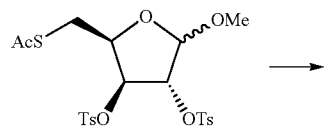

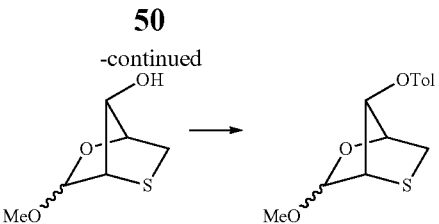

30.2 g of potassium carbonate was added to 463 mL of a methanol solution containing 119 g of S-(((2S,3S,4R)-5-methoxy-3,4-bis((4-methylphenyl)sulfonyloxy)tetrahydrofuran-2-yl)methyl) ethanethioate in a nitrogen atmosphere, followed by stirring for 1 hour at 25° C. and then for 1 hour at 60° C. The reaction mixture was cooled to 15° C., and 170 g of a 50% aqueous sodium hydroxide solution was added dropwise thereto at a temperature of equal to or lower than 25° C. The reaction mixture was stirred for 1 hour at 60° C. and then cooled to 10° C. Insoluble matters were removed by filtration, and the solvent was distilled away under reduced pressure. Toluene was added to the obtained residue, and the solvent was distilled away under reduced pressure, thereby obtaining 35.4 g of (1S,4S,7S)-3-methoxy-2-oxa-5-thiabicyclo[2.2.1]heptan-7-ol as a reddish brown oily substance.

213 mL of toluene, 1.82 g of tetrabutylammonium chloride, and 70.4 g of a 50% aqueous sodium hydroxide solution were added to the obtained (1S,4S,7S)-3-methoxy-2-oxa-5-thiabicyclo[2.2.1]heptan-7-ol. The mixture was cooled to 10° C. and stirred, and then 37.1 g of p-toluenesulfonyl chloride was added dropwise thereof in a state where the internal temperature was kept at a temperature of equal to or lower than 15° C. The mixture was heated to 25° C., and water and toluene were added thereto, followed by stirring for 3 hours at 25° C. Toluene and water were added to the reaction mixture. An organic layer was collected by separation, washed with a 25% aqueous sodium chloride solution, treated with 3 g of activated carbon, and then dried over anhydrous magnesium sulfate, and the solvent was distilled away under reduced pressure. As a result 38.6 g of (1S,4S,7S)-3-methoxy-2-oxa-5-thiabicyclo[2.2.1]heptan-7-yl 4-methylbenzoate as an orange oily substance was obtained.

$^1$H-NMR (CDCl$_3$) δ values: 7.94-7.89 (2H, m), 7.27-7.22 (2H, m), 5.58 (0.37H, t), 5.43 (0.63H, t), 5.34 (0.63H, d, J=2.4 Hz), 4.97 (0.37H, s), 4.74-4.71 (0.37H, m), 4.67-4.65 (0.63H, m), 3.81 (0.63H, t, J=2.4 Hz), 3.59 (0.37H, d, J=2.4 Hz), 3.54 (1.89H, s), 3.40 (1.11H, s), 3.09 (1.26H, d, J=1.5 Hz), 3.02-2.91 (0.74H, m), 2.41 (3H, s).

Example 20

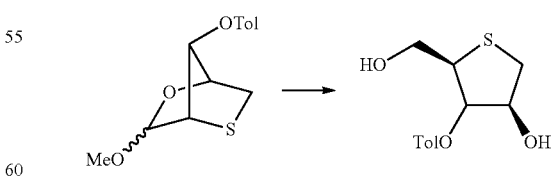

77 mL of 2 mol/L hydrochloric acid was added to 386 mL of a tetrahydrofuran solution containing 38.6 g of (1S,4S, 7S)-3-methoxy-2-oxa-5-thiabicyclo[2.2.1]heptan-7-yl 4-methylbenzoate, followed by stirring for 1 hour at 50° C. The reaction mixture was cooled to 5° C., 15.6 g of sodium hydrogen carbonate was added thereto, and then 104 g of sodium borohydride was added thereto in a state where the internal temperature was kept at a temperature of equal to or lower than 20° C. the reaction mixture was stirred for 10 minutes at a temperature of equal to or lower than 20° C. and then stirred for 1.5 hours at 25° C. The reaction mixture was cooled to 5° C., and 75 mL of 6 mol/L of hydrochloric acid was added dropwise thereto in a state where the internal temperature was kept at a temperature of equal to or lower than 20° C. Ethyl acetate and water were added to the reaction mixture. An organic layer was collected by separation, washed sequentially with a 25% aqueous sodium chloride solution, a mixed solution of a 7.5% aqueous sodium hydrogen carbonate solution and a 25% aqueous sodium chloride solution, and a 25% aqueous sodium chloride solution, and dried over anhydrous magnesium sulfate, and the solvent was distilled away under reduced pressure. 50 mL of ethyl acetate was added to the obtained residue and dissolved by heating, and then 100 mL of hexane was added thereto. Solids were collected by filtration, thereby obtaining 12.2 g (2R,3S,4S)-4-hydroxy-2-(hydroxymethyl)tetrahydrothiophen-3-yl 4-methylbenzoate as a white solid.

$^1$H-NMR (CDCl$_3$) δ values: 7.90 (2H, d, J=7.8 Hz), 7.25 (2H, d, J=7.8 Hz), 5.37 (1H, t, J=2.7 Hz), 4.55-4.47 (1H, m), 4.15-4.06 (1H, m), 4.03-3.97 (1H, m), 3.79-3.73 (1H, m), 3.69-3.66 (1H, m), 3.34-3.28 (1H, m), 3.08-3.02 (1H, m), 2.91 (1H, br), 2.42 (3H, s).

Example 21

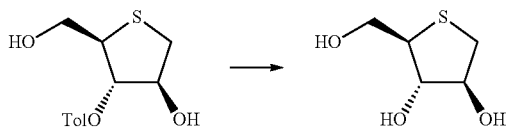

2.68 g of (2R,3S,4S)-4-hydroxy-2-(hydroxymethyl)tetrahydrothiophen-3-yl 4-methylbenzoate was dissolved in a mixed solution of 15 mL of methanol and 10 mL of tetrahydrofuran, and 58 mg of a 28% sodium methoxide/methanol solution was added thereto, followed by stirring for 4 hours at room temperature. The solvent was distilled away under reduced pressure. Ethyl acetate and water were added to the obtained residue. An aqueous layer was collected by separation and washed with ethyl acetate. An organic layer was extracted using water. The aqueous layer and the extract liquid were mixed together, and water was distilled away under reduced pressure, thereby obtaining 1.48 g of (2R,3S,4S)-2-(hydroxymethyl)tetrahydrothiophene-3,4-diol as a colorless oily substance.

$^1$H-NMR (DMSO-D$_6$) δ values: 5.12 (1H, d, J=4.5 Hz), 5.08 (1H, d, J=4.5 Hz), 4.82 (1H, t), 3.99-3.92 (1H, m), 3.76-3.68 (2H, m), 3.39-3.31 (1H, m), 3.11-3.04 (1H, m), 2.91-2.84 (1H, m), 2.59-2.52 (1H, m).

Example 22

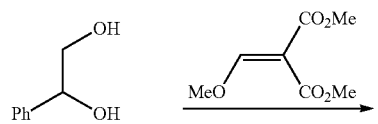

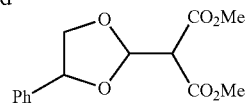

2.4 g of tert-butoxypotassium was added to 50 mL of a tetrahydrofuran solution containing 10 g of 1-phenylethane-1,2-diol and 10.2 g of dimethyl methoxymethylene malonate at 25° C., followed by stirring for 5.5 hours at 25° C. 40 mL of toluene was added to the reaction mixture, tetrahydrofuran was distilled away under reduced pressure, and then ethyl acetate and water were added thereto. An organic layer was collected by separation, washed sequentially with water, 1 mol/L hydrochloric acid, and a saturated aqueous sodium chloride solution, and dried over anhydrous magnesium sulfate, and the solvent was distilled away under reduced pressure. The obtained residue was purified by column chromatography, thereby obtaining 6.2 g of dimethyl-2-(4-phenyl-1,3-dioxolan-2-yl)malonate as a colorless oily substance.

$^1$H-NMR (CDCl$_3$) δ values: 7.39-7.33 (5H, m), 5.90 (0.5H, d, J=6.9 Hz), 5.73 (0.5H, d, J=6.9 Hz), 5.11 (1H, m), 4.44-4.25 (1H, m), 3.80-3.78 (6H, m), 3.77-3.72 (2H, m).

Example 23

(23-1)

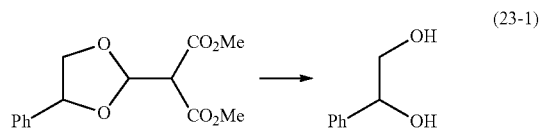 [SMILES: COC(=O)C(C(=O)OC)C1OCC(c2ccccc2)O1 ; OCC(O)c1ccccc1]

146 mg of diethylamine was added to a solution of 2 mL ethyl acetate and 2 mL of water containing 280 mg of dimethyl 2-(4-phenyl-1,3-dioxolan-2-yl)malonate at 25° C., followed by stirring for 2 hours at 25° C. An organic layer was collected by separation, washed sequentially with water, 1 mol/L hydrochloric acid, and a saturated aqueous sodium chloride solution, and dried over anhydrous magnesium sulfate, and the solvent was distilled away under reduced pressure.

As a result of measuring $^1$H-NMR of the obtained residue, it was confirmed that 1-phenylethane-1,2-diol was generated, and the reaction rate was 96%.

(23-2)

232 mg of a 28% sodium methoxide/methanol solution was added to 2 mL of a methanol solution containing 280 mg of dimethyl 2-(4-phenyl-1,3-dioxolan-2-yl)malonate at 25° C., followed by stirring for 3 hours at 25° C. Ethyl acetate and water were added to the reaction mixture. An organic layer was collected by separation, washed sequentially with water. 1 mol/L hydrochloric acid, and a saturated aqueous sodium chloride solution, and dried over anhydrous magnesium sulfate, and the solvent was distilled away under reduced pressure.

As a result of measuring $^1$H-NMR of the obtained residue, it was confirmed that 1-phenylethane-1,2-diol was generated, and the reaction rate was 100%.

(23-3)

166 mg of potassium carbonate was added to 2 mL of a methanol solution containing 280 mg of dimethyl 2-(4-phenyl-1,3-dioxolan-2-yl)malonate at 25° C., followed by stirring for 3 hours at 25° C. Ethyl acetate and water were added to the reaction mixture. An organic layer was collected by separation washed sequentially with water, 1 mol/L hydrochloric acid, and a saturated aqueous sodium chloride solution, and dried over anhydrous magnesium sulfate, and the solvent was distilled away under reduced pressure.

As a result of measuring $^1$H-NMR of the obtained residue, it was confirmed that 1-phenylethane-1,2-diol was generated and the reaction rate was 93%.

(23-4)

100 mg of a sodium hydrogen carbonate was added to 2 mL of a methanol solution containing 280 mg of dimethyl 2-(4-phenyl-1,3-dioxolan-2-yl)malonate at 25° C., followed by stirring for 3 hours at 25° C. Ethyl acetate and water were added to the reaction mixture. An organic layer was collected by separation, washed sequentially with water, 1 mol/L hydrochloric acid, and a saturated aqueous sodium chloride solution, and dried over anhydrous magnesium sulfate, and the solvent was distilled away under reduced pressure.

As a result of measuring $^1$H-NMR of the obtained residue, it was confirmed that 1-phenylethane-1,2-diol was generated, and the reaction rate was 92%.

The compound of the present invention is useful as an intermediate for manufacturing salacinol useful as a bioactive substance, and the manufacturing method of the present invention is useful as a method for manufacturing salacinol.

What is claimed is:

1. A method for manufacturing salacinol, comprising: obtaining a compound represented by Formula (1b) by reacting a compound represented by Formula (1a) with a compound represented by Formula (7),

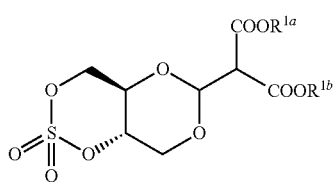
(1a)

(in the formula, each of $R^{1a}$ and $R^{1b}$ are the same as or different from each other and each represent a hydrogen atom or a carboxy protective group),

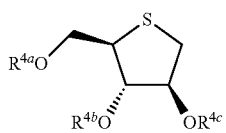
(7)

(in the formula, each of $R^{4a}$, $R^{4b}$, and $R^{4c}$ are the same as or different from each other and each represent a hydrogen atom or a hydroxy protective group), and

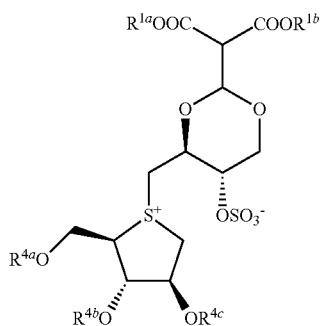
(1b)

(in the formula, each of $R^{1a}$, $R^{1b}$, $R^{4a}$, $R^{4b}$, and $R^{4c}$ has the same definition as described above); and then subjecting the compound represented by Formula (1b) to a deprotection reaction.

2. The manufacturing method according to claim 1, wherein each of $R^{1a}$ and $R^{1b}$ is a carboxy protective group, and each of $R^{4a}$, $R^{4b}$, and $R^{4c}$ is a hydrogen atom.

3. A method for manufacturing salacinol, comprising: obtaining a compound represented by Formula (1c) by reacting a compound represented by Formula (8) with a compound represented by Formula (9),

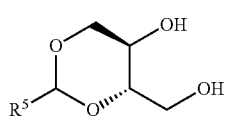
(8)

(in the formula, $R^5$ is an aryl group which may be substituted),

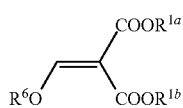
(9)

(in the formula, $R^{1a}$ and $R^{1b}$ are the same as or different from each other and each represent a hydrogen atom or a carboxy protective group; $R^6$ is a $C_{1-6}$ alkyl group which may be substituted), and

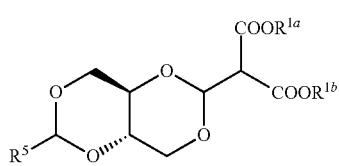
(1c)

(in the formula, each of $R^{1a}$, $R^{1b}$, and $R^5$ has the same definition as described above);

then obtaining a compound represented by Formula (1d) by subjecting the compound represented by Formula (1c) to a deprotection reaction,

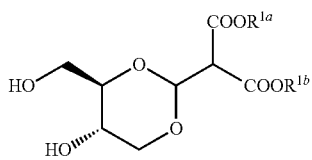

(1d)

(in the formula, each of $R^{1a}$ and $R^{1b}$ has the same definition as described above);

then obtaining a compound represented by Formula (1a) by reacting the compound represented by Formula (1d) with a sulfur-containing compound and then subjecting the resulting compound to an oxidation reaction if necessary,

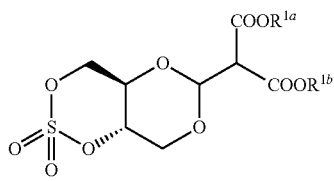

(1a)

(in the formula, each of $R^{1a}$ and $R^{1b}$ has the same definition as described above);

then obtaining a compound represented by Formula (1b) by reacting the compound represented by Formula (1a) with a compound represented by Formula (7),

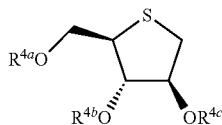

(7)

(in the formula, $R^{4a}$, $R^{4b}$, and $R^{4c}$ are the same as or different from each other and each represent a hydrogen atom or a hydroxy protective group), and

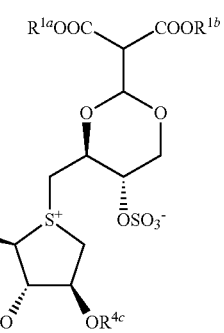

(1b)

(in the formula, each of $R^{1a}$, $R^{1b}$, $R^{4a}$, $R^{4b}$, and $R^{4c}$ has the same definition as described above); and then subjecting the compound represented by Formula (1b) to a deprotection reaction.

4. The manufacturing method according to claim 3, wherein $R^5$ is a phenyl group which may be substituted.

5. The manufacturing method according to claim 3, wherein each of $R^{1a}$ and $R^{1b}$ is a carboxy protective group, and each of $R^{4a}$, $R^{4b}$, and $R^{4c}$ is a hydrogen atom.

\* \* \* \* \*